United States Patent
Godfrin et al.

(10) Patent No.: US 10,046,009 B2
(45) Date of Patent: Aug. 14, 2018

(54) METHOD OF TREATMENT USING A PHARMACEUTICAL COMPOSITION COMPRISING ERYTHROCYTES ENCAPSULATING A PLP-DEPENDENT ENZYME AND ITS COFACTOR

(71) Applicant: ERYTECH PHARMA, Lyons (FR)

(72) Inventors: Yann Godfrin, Lyons (FR); Vanessa Bourgeaux, Lyons (FR); Fabien Gay, Lyons (FR); Thomas Cortese, Labege (FR)

(73) Assignee: ERYTECH PHARMA, Lyon (FR)

( * ) Notice: Subject to any disclaimer, the term of this patent is extended or adjusted under 35 U.S.C. 154(b) by 0 days.

(21) Appl. No.: 15/117,588

(22) PCT Filed: Feb. 12, 2015

(86) PCT No.: PCT/EP2015/052962
§ 371 (c)(1),
(2) Date: Aug. 9, 2016

(87) PCT Pub. No.: WO2015/121348
PCT Pub. Date: Aug. 20, 2015

(65) Prior Publication Data
US 2016/0361361 A1 Dec. 15, 2016

(30) Foreign Application Priority Data
Feb. 12, 2014 (FR) ...................... 14 51100

(51) Int. Cl.
| A61K 31/675 | (2006.01) |
| A61K 35/18 | (2015.01) |
| A61K 38/51 | (2006.01) |
| A61K 9/50 | (2006.01) |
| A61K 38/45 | (2006.01) |
| C12N 9/88 | (2006.01) |
| A61K 35/12 | (2015.01) |

(52) U.S. Cl.
CPC ............ *A61K 35/18* (2013.01); *A61K 9/5068* (2013.01); *A61K 31/675* (2013.01); *A61K 38/45* (2013.01); *A61K 38/51* (2013.01); *C12N 9/88* (2013.01); *C12Y 206/01005* (2013.01); *C12Y 404/01011* (2013.01); *A61K 2035/124* (2013.01)

(58) Field of Classification Search
None
See application file for complete search history.

(56) References Cited

U.S. PATENT DOCUMENTS

| 6,475,767 B1 | 11/2002 | Akita et al. |
| 8,617,840 B2 | 12/2013 | Godfrin et al. |
| 8,852,880 B2 | 10/2014 | Godfrin |
| 8,974,802 B2 | 3/2015 | Dufour et al. |
| 9,125,876 B2 | 9/2015 | Godfrin et al. |
| 9,364,504 B2 | 6/2016 | Godfrin et al. |
| 9,580,739 B2 | 2/2017 | Godfrin |
| 2002/0111310 A1* | 8/2002 | Meyers ................ C12N 9/1096 435/193 |
| 2008/0261262 A1 | 10/2008 | Godfrin |
| 2008/0274092 A1 | 11/2008 | Godfrin et al. |
| 2010/0310612 A1 | 12/2010 | Dufour et al. |
| 2010/0316620 A1 | 12/2010 | Bourgeaux et al. |
| 2011/0014171 A1 | 1/2011 | Bourgeaux et al. |
| 2012/0009140 A1 | 1/2012 | Godfrin et al. |
| 2012/0121570 A1 | 5/2012 | Godfrin |
| 2012/0129210 A1 | 5/2012 | Bourgeaux et al. |
| 2012/0207745 A1 | 8/2012 | Godfrin et al. |
| 2014/0010795 A1 | 1/2014 | Bourgeaux et al. |
| 2014/0154797 A1 | 6/2014 | Godfrin et al. |
| 2014/0363413 A1 | 12/2014 | Bourgeaux et al. |
| 2015/0071894 A1 | 3/2015 | Godfrin |
| 2015/0086521 A1 | 3/2015 | Godfrin |
| 2016/0030532 A1 | 2/2016 | Godfrin et al. |
| 2016/0095884 A1 | 4/2016 | Godfrin et al. |
| 2016/0120956 A1 | 5/2016 | Godfrin et al. |
| 2016/0324946 A1 | 11/2016 | Godfrin et al. |
| 2016/0361361 A1 | 12/2016 | Godfrin et al. |

OTHER PUBLICATIONS

Cheng, C. et al. Higher Plasma Pyridoxal Phosphate is Associated with Increased Antioxidant Enzyme Activities in Critically Ill Surgical Patients. BioMed Research Int ID 572081, 8 pages, 2013.*
Koutmos M. et al. Structural Basis for Substrate Activation and Regulation by Cystathionine Beta-Synthase Domains in Cystathionine Beta-Synthase. PNAS 107(49)20958-63, Dec. 7, 2010.*
Mozzarelli A. et al. Exploring the Pyridoxal 5'-Phosphate Dependent Enzymes. The Chemical Record 6:275-287, 2006.*
Sato D. et al. Methionine Gamma Lyase: The Unique Reaction Mechanism, Physiological Roles, and Therapeutic Applications . . . Life 61(11)1019-1028, Nov. 2009.*
International Search Report dated Apr. 23, 2015 in International Application No. PCT/EP2015/052962.
Agrawal, et al., "Targeting methionine auxotrophy in cancer: discover & exploration", 2012, pp. 53-61, vol. 12, No. 1, Expert Opin. Biol. Ther., XP009180552.
Sun, et al., "In Vivo Efficacy of Recombinant Methioninase Is Enhanced by the Combination of Polyethylene Glycol Conjugation and Pyridoxal 5'-Phosphate Supplementation", Dec. 1, 2003, pp. 8377-8383, vol. 63, Cancer Research, XP-002391476.
El-Sayed, et al., "PLP-Dependent Enzymes: a Potent Therapeutic Approach for Cancer and Cardiovascular Diseases", Aug. 23, 2011, pp. 119-136, Targets in Gene Therapy, XP055143288.
Bax, et al., "A 9-year evaluation of carrier erythrocyte encapsulated adenosine deaminase (ADA) therapy in a patient with adult-type ADA deficiency", Oct. 1, 2007, pp. 338-348, vol. 79, No. 4, European Journal of Haematology, XP002687579.

(Continued)

*Primary Examiner* — Ralph J Gitomer
(74) *Attorney, Agent, or Firm* — B. Aaron Schulman, Esq.; Stites & Harbison PLLC

(57) ABSTRACT

The invention relates to a pharmaceutical composition containing a PLP-dependent enzyme and optionally its cofactor, pyridoxal phosphate (PLP), and/or a phosphate or non-phosphate precursor of PLP, its use as a drug, its production method and a therapeutic treatment method related to it. The pharmaceutical composition comprises erythrocytes and a pharmaceutically acceptable vehicle, the erythrocytes encapsulating the PLP-dependent enzyme. The PLP-dependent enzyme may be methioninase, tyrosine phenol-lyase, tyrosine aminotransferase or cystathionine beta-synthase.

15 Claims, 7 Drawing Sheets

(56) References Cited

OTHER PUBLICATIONS

Figure 1:
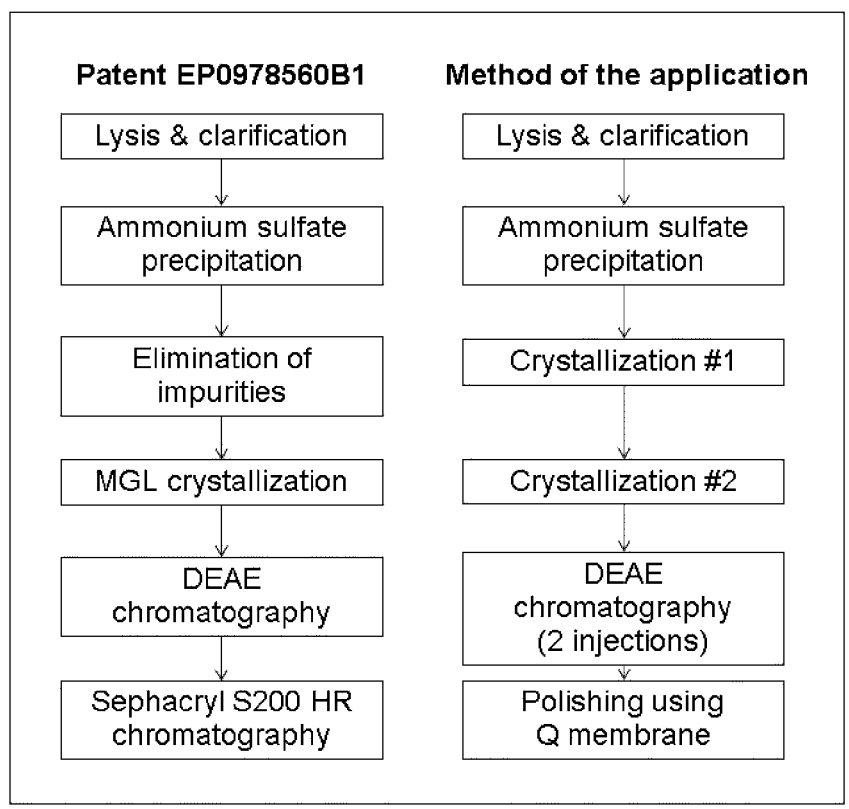

Yang, et al., "PEGylation Confers Greatly Extended Half-Life and Attenuated Immunogenicity Recombinant Methioninase in Primates", Sep. 15, 2007, pp. 6673-6678, vol. 64, No. 15, Cancer Research, XP003025733.

Millan, et al., "Drug, enzyme and peptide delivery using erythrocytes as carriers", Feb. 20, 2004, pp. 27-49, vol. 95, No. 1, Journal of Controlled Release, XP004487812.

Moran, et al., "Carrier erythrocyte entrapped thymidine phosphorylase therapy for MNGIE", Aug. 26, 2008, pp. 686-688, vol. 71, No. 9, Neurology, XP002687578.

Godfrin, et al., "Red Blood Cells for a New Drug Formulation", Jun. 7, 2012, XP055144189, Retrieved from the Internet Oct. 2, 2014: URL: http://c.ymcdn.com/sites/www.celltherapysociety.org/resource/resmgr/uploads/files/AnnualMeetings/2012/FinalPresentationsPDF/Thurs1530.3GodfrinGrandB.pdf.

Ravilla, et al., Erythrocytes as Carrier for Drugs, Enzymes and Peptides, Apr. 28, 2012, pp. 166-176, vol. 2, No. 4, Journal of Applied Pharmaceutical Science, XP055143753.

Anderson, et al., "Conversion of Vitamin B6 Compounds to Active Forms in the Red Blood Cell", 1971, pp. 1901-1909, vol. 50, The Journal of Clinical Investigation.

El-Sayed, et al., "Microbial L-methioninase: production, molecular characterization, and therapeutic applications", 2010, pp. 445-467, vol. 86, Appl Microbiol Biotechnol.

Kumagai, et al "Tyrosine Phenol Lyase II. Cofactor Requirements", Apr. 10, 1970, pp. 1773-1777, vol. 245, No. 7, The Journal of Biological Chemistry.

Kraus, et al., "Purification and Properties of Cystathionine ß-Synthase from Human Liver", Sep. 25, 1978, pp. 6523-6528, vol. 253, No. 18, The Journal of Biological Chemistry.

Kumagai, et al., "Tyrosine Phenol Lyase I. Purification, Crystallization, and Properties", Apr. 10, 1970, pp. 1767-1772, vol. 245, No. 7, The Journal of Biological Chemistry.

Rettenmeier, et al., "Isolation and characterization of the human tyrosine aminotransferase gene", 1990, pp. 3853-3861, vol. 18, No. 13, Nucleic Acids Research.

Percudani, et al., "A genomic overview of pyridoxal-phosphate-dependent enzymes", 2003, pp. 850-854, vol. 4, No. 9, EMBO reports.

Durando, et al, "Dependance en methionine des cellules cancereuses: une nouvelle approche therapeutique?", 2008, pp. 69-76, vol. 95, No. 1, Bull Cancer.

Yang, et al., "Pharmacokinetics, Methionine Depletion, and antigenicity of Recombinant Methioninase in Primates", Mar. 15, 2004, pp. 2131-2138, vol. 10, Clinical Cancer Research.

Gay, et al., "Methionine tumor starvation by erythrocyte-encapsulated methionine gamma-lyase activity controlled with per os vitamin B6", 2017, pp. 1-16, Cancer Medicine.

Elmer, et al, "Increased Tyrosine Phenol-Lyase Activity in Mice following Pyridoxal Phosphate Administration", Nov. 1978, pp. 3663-3667, vol. 38, Cancer Research.

* cited by examiner

METHOD OF TREATMENT USING A PHARMACEUTICAL COMPOSITION COMPRISING ERYTHROCYTES ENCAPSULATING A PLP-DEPENDENT ENZYME AND ITS COFACTOR

This Application is a National Stage Entry of, and claims priority to, International Application No. PCT/EP2015/052962, filed Feb. 12, 2015, which claims priority to French Patent Application No. FR1451100, filed on Feb. 12, 2014.

The invention relates to a pharmaceutical composition containing a PLP-dependent enzyme, for example methioninase, and optionally its cofactor, pyridoxal phosphate (PLP or P5P), and/or a phosphate or non-phosphate precursor of PLP, to its use as a drug, to its production method and to a therapeutic treatment method relating to it.

Pyridoxal phosphate (PLP), a derivative of vitamin B6, is a cofactor used for a large variety of enzymes. Called herein "PLP enzymes" for PLP-dependent enzymes, they form a group of about 145 distinct enzymes involved for most of them in metabolic pathways for transforming amino acids. The reaction catalyzed by these enzymes includes decarboxylations, transaminations or further removal reactions (Percudani and Perrachi, EMBO reports Vol. 4 no. 9, 2003).

Because of the large number of enzymes belonging to the group of PLP enzymes and of reactions catalyzed by the latter, their potential use in human therapeutics has been investigated. From among the different opportunities for therapeutic intervention associated with PLP enzymes, their use in the treatment of cancer and of cardiovascular pathologies has been the subject of many studies (El-Sayed and Shindia "Targets in gene therapy" Prof. Yongping You ed., 2011). More particularly, methioninase would be of interest for depleting plasma methionine and inducing apoptosis of auxotrophic tumoral cells for this amino acid. It was shown that many human tumoral cells were incapable of proliferating when methionine is replaced with its precursor homocysteine while normal cells have the capability of proliferating in such a medium. This dependency on methionine was notably observed for cell lines derived from breast, lung, colon, kidney, bladder, melanoma and glioblastoma cancers (Durando et al., Bull Cancer 2008; 95 (1): 69-76).

In spite of the therapeutic interest of the PLP enzymes, development of treatment based on an administration via a systemic route of these enzymes comes up against significant limitations:
- the PLP enzymes are mainly obtained from prokaryotic organisms and are therefore strongly immunogenic in the case of administration to humans
- their half-life in plasma is short, requiring resorting to frequent administrations or to large doses in order to be able to obtain sufficient activity
- the low bioavailability of the PLP cofactor in plasma causes a rapid drop of their activity after administration.

These limitations were widely described in the case of methioninase. Sun et al. have produced a recombinant methioninase in the *Escherichia coli* bacterium from the gene coding for the enzyme extracted from the *Pseudomonas putida* bacterium. The thereby obtained enzyme called rMETase was injected intravenously to immunodeficient mice. Twenty four hours after injection, the plasma activity of the enzyme, determined in vitro without adding PLP, was undetectable, indicating its short action period (Sun et al. Cancer Research, 8377-8383, 2003).

A year later, the same team published the results of administration of rMETase in macaques (Yang et al. Clinical Cancer Research Vol. 10, 2131-2138, 2004). In this study, rMETase doses of 1,000, 2,000 and 4,000 units/kg were administered intravenously to six monkeys. A second injection was performed 28 days after the first and caused in two monkeys an anaphylactic shock causing the death of one of the two animals. The immunogenicity of rMETase moreover caused the development of anti-rMETase antibodies of the IgG type (a majority) and of the IgM type for the majority of the treated animals (four out of six). The neutralizing nature of these antibodies was demonstrated in vitro.

In order to overcome the short half-life and immunogenicity limitations of their methioninase, the same authors then proposed resorting to pegylation of their enzyme. The grafting of PEG groups is a known technique for increasing the half-life and reducing the immunogenicity of therapeutic proteins. Activated PEG derivatives were put into the presence of rMETase in order to obtain PEG-rMETase. This modification of the enzyme caused an increase in the half-life in mice from 2 h for the free enzyme to 38 h for the PEG-rMETase. This significant increase in half-life is accompanied with a reduction in immunogenicity (Sun et al. Cancer Research 63, 8377-8383, 2003).

If pegylation partly met the problems of half-life and immunogenicity, a major problem of PLP enzymes remains: the low bioavailability of the cofactor in the plasma. The PLP enzymes are catalytically active in the presence of their cofactor, PLP, this is then referred to as a holoenzyme. After injection, the holoenzyme is rapidly converted into an inactive apoenzyme because of the loss of the PLP cofactor.

PLP brought in an exogenous way is rapidly unavailable for the enzyme, the plasma half-life of the free PLP only being about 15 minutes. This phenomenon was demonstrated in the case of the PLP enzyme, tyrosine phenol-lyase (TPL). Elmer et al. (Cancer Research 38; 3663-3667, 1978) purified TPL and injected it into normal mice. Five hours after the injection, blood samples were taken in order to assay the activity of the TPL. This activity assay was carried out according to two conditions: a portion of the samples were assayed without adding PLP, the other portion was assayed with addition of an optimal amount of PLP in the reaction mixture for the assay (both of these conditions reflecting the actually measured activity in plasma and the potential activity of the enzyme if it had access to its PLP cofactor). The comparison of the obtained results shows that only 7% of the potential activity of the TPL is actually measured in the plasma. The same test was conducted with a group of mice, wherein, concomitantly to the injection of TPL, a large amount of PLP was administered, and then re-injections of PLP were carried out every hour. In this scenario, the comparison of the assay results shows that 37% of the potential activity is actually measured in the plasma. Co-administration of PLP therefore gave the possibility of improving in a limited way the activity of TPL in plasma. However, PLP provided in an exogenous way is rapidly unavailable for TPL, the plasma half-life of free PLP being of about 15 minutes. Therefore, the rise in the plasma level of PLP by repeated injections of PLP in solution is not feasible. Elmer et al. proposed provision of PLP in a prolonged way over time via an implant consisting of spermaceti and groundnut oil injected via an intramuscular route at the hip. Nevertheless, this solution was not found to be convincing, it does not manage to re-establish the activity actually measured in plasma beyond 25% of the potential activity and it does not improve in a statistically significant way the anti-tumoral effect of TPL in mice implanted with a melanoma B-16 tumor. Similar observations were made with methioninase. Sun et al. (Cancer Research 63, 8377-

8383, 2003) ascertain that in vitro, the holoenzyme PLP-rMETase is relatively stable but that in vivo, this complex is rapidly dissociated leading to a loss of activity of the rMETase. The authors further show that the methionine depletion duration obtained with rMETase as well as with PEG-rMETase may be improved by a PLP supplement via the implantation of a PLP pump (a pump continuously administering PLP). Nevertheless, this continuous administration device will invariably be confronted with the problem of the low bioavailability of PLP in plasma.

Therefore, although the therapeutic potential of the PLP enzymes has been the subject of much research work, in particular having led for methioninase to conducting pilot clinical trials, no demonstration of the clinical efficiency of these enzymes was able to be provided.

Thus, with the purpose of utilizing the therapeutic potential of PLP enzymes, it would be advantageous to have a solution allowing these enzymes to be maintained in the presence of an optimum and available amount of PLP.

Various methods have been described for allowing incorporation of active ingredients in erythrocytes. Among these methods, the so-called lysis-resealing technique is the most widespread. This technique comprises three alternatives, which are hypotonic dialysis, hypotonic <<preswelling>> and hypotonic dilution, all based on the difference in osmotic pressure between the inside and the outside of the erythrocytes. These alternatives have in common the five following steps: packed Red Blood Cells are washed and centrifuged one or several times with a physiological buffer, the erythrocytes are put into contact with a hypotonic liquid medium resulting in the opening of pores in the erythrocyte membrane, the active ingredient enters the erythrocytes, the pores are closed (<<resealed>>) by means of a hypertonic buffer, confining the active ingredient inside the erythrocytes, and the latter are then suspended in a preservation solution. Hypotonic dialysis technique is the most interesting technique and has been the subject of industrial developments. The one described in EP 1 773 452 is the most performing at the present time, it has the advantage of being reproducible and of improving the encapsulation rate of the active ingredient.

The encapsulation of enzymes in erythrocytes, with view to limiting the risks related to immunogenicity of the enzyme, to extending its half-life, was already proposed in research work which was the subject of scientific publications. Encapsulation of an enzyme, L-asparaginase, was described in EP 1 773 452, as well as arginine deiminase in EP 1 874 341.

The previous studies do not relate to an enzyme requiring a cofactor and do not tackle the complexity related to the kinetics of a PLP enzyme and of its PLP cofactor.

An objective of the invention is to provide a pharmaceutical composition containing a PLP enzyme, which allows limitation of the risks related to the immunogenicity of the enzyme, extension of its half-life, while putting the enzyme in the presence of an optimal and available amount of its PLP cofactor.

The object of the invention is thus a suspension of erythrocytes in a pharmaceutically acceptable vehicle or a pharmaceutical composition comprising erythrocytes and a pharmaceutically acceptable vehicle, the erythrocytes encapsulating a PLP enzyme. This will be hereafter referred to as a composition in order to equally refer to the suspension and the pharmaceutical composition. By <<encapsulating>> is meant that the active ingredient (enzyme and optionally cofactor and/or other molecule) is essentially or totally present inside. <<Essentially>> means that a minority proportion of the active ingredient may nevertheless be found trapped in the membrane.

The composition notably contains from 0.01 to 30, preferably from 0.05 to 10 mg of PLP enzyme per ml of red blood cells.

According to a first embodiment, the PLP enzyme is methioninase, further called, inter alia, L-methioninase, Methionine Gamma Lyase MGL, number EC 4.4.1.11, CAS number 42616-25-1. In order to be aware of the methioninase sources which may be used according to the invention, mention may notably be made to the publication El Sayed A, Applied Microbiol. Biotechnol. (2010) 86: 445-467.

According to a second embodiment, the PLP enzyme is Tyrosine Phenol-Lyase or TPL, EC 4.1.99.2, CAS 9059-31-8. Reference may be made to H. Kumagai et al., J. Biol. Chem. 245, 7: 1767-72 and 245, 7: 1773-7.

According to a third embodiment, the PLP enzyme is tyrosine aminotransferase (hTATase), EC 2.6.1.5, CAS 9014-55-5. Reference may be made to R. Rettenmeier et al., Nucleic Acids Res. 1990, 18, 13: 3583-61.

According to a fourth embodiment, the PLP enzyme is cystathionine beta-synthethase or synthase, EC 4.2.1.22, CAS 9023-99-8. Reference may be made to J. Kraus et al., J. Biol. Chem. 1978, 253, 18: 6523-8.

The composition may further comprise the cofactor of the enzyme, i.e. PLP, and/or a precursor thereof, which may be a non-phosphate precursor, such as a non-phosphate form of vitamin B6, and/or a phosphate precursor such as pyridoxine phosphate (PNP).

Vitamin B6 exists in different forms, either phosphate or non-phosphate. Pyridoxine phosphate (PNP), pyridoxal phosphate (PLP) and pyridoxamine phosphate (PMP) are the phosphate forms thereof. The corresponding non-phosphate forms are pyridoxine (PN), pyridoxal (PL), and pyridoxamine (PM). The non-phosphate forms of vitamin B6 may cross the erythrocyte membrane, which the phosphate forms can only cross with difficulty. According to the predominant route (as described by Anderson et al. J. Clin. Invest. 1971, Vol. 50, 1901-1909), pyridoxine (PN) is transformed inside the erythrocytes into PNP under the effect of PN-kinase, PNP is then transformed into PLP under the effect of PNP-oxidase. The PLP may then be transformed into pyridoxal (PL) under the effect of PLP-phosphatase and the PL may leave the erythrocytes. It is easily understood that the provided precursor is able to undergo transformations in the erythrocytes during the preparation method or during the storage of the composition.

By a non-phosphate form of vitamin B6, will be meant here one of the three "vitamers" of vitamin B6 or a mixture of two or three vitamers: PL, PN and PM. The PN form is preferred. They may also be in the form of a salt.

The composition comprises PLP encapsulated in erythrocytes. The PLP may be provided during the encapsulation procedure or be totally or partly obtained in the erythrocytes from its precursor. The PLP either present or formed may be associated with the enzyme. The composition may therefore comprise the corresponding holoenzyme, for example methioninase-PLP. Under these conditions, the half-life of the active enzyme, as observed for example with the duration of the plasma depletion of its substrate, is considerably increased. The composition according to the invention notably gives the possibility of preserving enzymatic activity beyond 24 hours after administration, notably at or beyond 1, 5, 10 or 15 days. By enzymatic activity is notably meant a depletion of more than 20, 30, 40 or 50% of the substrate in the plasma.

In an embodiment, the composition therefore comprises pyridoxal phosphate (PLP) and/or a non-phosphate form of vitamin B6 and/or a phosphate precursor, pyridoxine phosphate (PNP) and/or pyridoxamine phosphate (PMP).

According to a feature, PNP and/or PMP is encapsulated inside the erythrocytes within the composition. This precursor may be co-encapsulated with the enzyme or be totally or partly obtained in the erythrocytes from its own precursor.

The composition notably comprises from about 0.05 to about 600, notably from about 0.5 to about 100, preferably from about 5 to about 50 µmoles of PLP and/or PNP and/or PMP, encapsulated per liter (L) of red blood cells.

According to a feature, the composition comprises erythrocytes encapsulating the PLP enzyme and PLP and further a non-phosphate PLP precursor, encapsulated in the erythrocytes, present inside the erythrocytes or present inside and outside the erythrocytes. This non-phosphate precursor may be PN, PL or PM, preferably PN, or a mixture of two or three of these compounds. The non-phosphate precursor may be present inside and/or outside the erythrocytes. The presence of this non-phosphate precursor gives the possibility of reaching a remarkably higher intra-erythrocyte PLP level than in the absence of this non-phosphate precursor.

In an embodiment, the composition comprises erythrocytes encapsulating the PLP enzyme and in addition PLP and one of its phosphate precursors, PNP, PLP and/or PMP. This same composition may further comprise advantageously a non-phosphate precursor, notably PN, as this has just been described.

The compositions according to the invention preferably have a hematocrit greater than or equal to 35%, 40% or 45%.

According to an embodiment, the composition comprises erythrocytes and a pharmaceutically acceptable vehicle, the erythrocytes encapsulating the PLP enzyme, e.g. methioninase, on the one hand, and, vitamin B6 in a non-phosphate form, preferably PN, on the other hand, for simultaneous, separate or sequential administration. The composition may notably be in the form of a kit, comprising separately the erythrocytes (suspension) and the vitamin B6 in a non-phosphate form, preferably PN (solution). According to an embodiment, the pharmaceutically acceptable vehicle is a <<preservation solution>> for erythrocytes, i.e. a solution in which the erythrocytes encapsulating an active ingredient are suspended in their suitable form for being stored while awaiting their injection. A preservation solution preferably comprises at least one agent promoting preservation of the erythrocytes, notably selected from glucose, dextrose, adenine and mannitol. Advantageously, the preservation solution contains inorganic phosphate allowing inhibition of the intra-erythrocyte PLP-phosphatase enzyme.

The preservation solution may be an aqueous solution comprising NaCl, adenine and at least one compound from among glucose, dextrose and mannitol. According to a feature, it further comprises an inorganic phosphate.

The preservation solution may comprise NaCl, adenine and dextrose, preferably an AS3 medium. According to a feature, it further comprises an inorganic phosphate.

The preservation solution may comprise NaCl, adenine, glucose and mannitol, preferably a SAG-Mannitol or ADsol medium. According to a feature, it further comprises an inorganic phosphate.

In particular, the composition or suspension, in a preservation solution, is characterized by an extracellular hemoglobin level maintained at a level equal to or less than 0.5, in particular 0.3, notably 0.2, preferably 0.15, even better 0.1 g/dl at 72 h and preservation at a temperature comprised between 2 and 8° C.

In particular, the composition or suspension, in a preservation solution, is characterized by an extracellular hemoglobin level maintained at a level equal to or less than 0.5, in particular 0.3, notably 0.2, preferably 0.15, even better 0.1 g/dl for a period comprised between 24 h and 20 days, notably between 24 and 72 h and preservation at a temperature comprised between 2 and 8° C.

The extracellular hemoglobin level is advantageously measured by the manual reference method described in G. B. Blakney and A. J. Dinwoodie, Clin. Biochem. 8, 96-102, 1975. Automatic devices also exist which allows this measurement to be made with a sensitivity which is specific to them.

In particular, the composition or suspension, in a preservation solution, is characterized by a hemolysis rate maintained at equal to or less than 2, notably 1.5, preferably 1% at 72 h and preservation at a temperature comprised between 2 and 8° C.

In particular, the composition or suspension, in a preservation solution, is characterized by a hemolysis rate maintained at equal to or less than 2, notably 1.5, preferably 1% for a period comprised between 24 h and 20 days, notably between 24 and 72 h and at a temperature comprised between 2 and 8° C.

In particular, the hematocrit of the suspension is equal to or greater than 35%, 40%, 45%.

According to a particular method, the metabolism of vitamin B6 in erythrocytes is modified so as to increase the intra-erythrocyte PLP concentration by increasing the intra-erythrocyte levels of PN-kinase and PNP-oxidase and/or by reducing the intra-erythrocyte level of PLP-phosphatase.

According to a characteristic, the composition comprises, in addition to the PLP enzyme, e.g. methioninase, and to PLP or a precursor thereof, PN-kinase and/or PNP-oxidase and/or an agent inhibiting PLP-phosphatase. These enzymes or agents may be found encapsulated in the erythrocytes or be found outside and inside the erythrocytes.

This (these) enzymes or agents may also be administered separately, by notably being mixed with the formulation of non-phosphate vitamin B6 when it is separated from the suspension of erythrocytes.

The object of the invention is thus such compositions for use as a drug.

The object of the invention is notably a drug giving the possibility of providing to a patient in need thereof, a PLP enzyme and its cofactor, under conditions of good bioavailability, which means that the enzyme and its cofactor are available for each other and in an effective amount so that the enzyme is active and efficient in a therapeutic application. The drug notably aims at depleting or reducing the plasma or circulating concentration and/or the concentration at an organ, of a substrate of the enzyme.

According to a first sub-object, the drug comprises methioninase and allows depletion or reduction of the plasmatic or circulating methionine in a patient in need thereof. The drug is an anticancer drug, it allows treatment of a cancer, notably a cancer comprising tumoral cells auxotrophic for methionine, notably breast, lung, colon, kidney, bladder, melanoma and glioblastoma cancers.

According to a second sub-object, the drug comprises methioninase and allows depletion or reduction of the plasmatic or circulating or hepatic homocysteine in a patient in need thereof. The drug allows treatment of homocysteinuria and/or hyperhomocysteinemia and/or associated pathologies, such as a cardiovascular disease, of the central nervous system, of the ocular system and/or of the skeleton (El-Sayed and Shindia Targets in gene therapy Prof. Yongping You ed., 2011).

According to third sub-object of the invention, the drug contains TPL and allows depletion or reduction of the plasmatic or circulating tyrosine in a patient in need thereof. The drug is an anticancer drug, it allows treatment of a cancer, notably a cancer comprising tumoral cells auxotrophic for tyrosine, notably melanoma.

According to a fourth sub-object of the invention, the drug contains hTATase and allows depletion or reduction of the plasmatic or circulating and/or hepatic tyrosine in a patient in need thereof. The drug allows treatment of a rare disease related to a deficiency in this PLP enzyme, notably the Richner-Hanhart syndrome (tyrosinemia of type II).

According to a fifth sub-object of the invention, the drug contains cystathionine beta-synthase and allows depletion or reduction of the plasmatic or circulating and/or hepatic homocysteine in a patient in need thereof. The drug allows treatment of homocysteinuria and/or hyperhomocysteinemia and/or associated pathologies, such as a cardiovascular disease, a disease of the central nervous system, a disease of the ocular system and/or a disease of the skeleton.

The invention also relates to a method for preparing a pharmaceutical composition comprising erythrocytes encapsulating a PLP enzyme, e.g. methioninase, a pharmaceutically acceptable vehicle, and pyridoxal phosphate (PLP) and optionally a phosphate or non-phosphate PLP precursor, a method comprising the following steps: optionally, and preferably, a pellet of red blood cells is washed and centrifuged one or several times with a physiological buffer; the erythrocyte suspension is put into contact with a hypotonic liquid medium resulting in the opening of pores in the erythrocyte membrane; the erythrocyte suspension is then put into contact with the PLP enzyme, e.g. methioninase, before and after opening the pores; the PLP enzyme, e.g. methioninase, enters the erythrocytes; the pores are closed by means of an isotonic or hypertonic, advantageously hypertonic buffer, and a suspension of resealed erythrocytes containing the PLP enzyme, e.g. methioninase, is collected; optionally the erythrocyte suspension is incubated for removing the most fragile erythrocytes; the erythrocyte suspension is washed and conditioned with a preservation solution; a method wherein:
  PLP and/or, if present, a PLP phosphate precursor, is co-encapsulated with the PLP enzyme, e.g. methioninase,
  if present, the non-phosphate PLP precursor is added to the suspension of erythrocytes before and/or after opening the pores, and/or
  if present, the non-phosphate PLP precursor is added during incubation or to the preservation solution.

Preferably, some PLP is co-encapsulated with the PLP enzyme and at least one non-phosphate precursor, such as PN, PL and/or PM, is added to the erythrocyte suspension before and/or after opening the pores, and/or during incubation and/or to the preservation solution. Preferably, the non-phosphate precursor is PN.

The erythrocyte suspension is put into contact with a hypotonic liquid medium resulting in the opening of pores in the erythrocyte membrane. It is seen that there exist three alternatives in the lysis-resealing technique, which are hypotonic dialysis, hypotonic preswelling and hypotonic dilution, all based on the difference in osmotic pressure between the inside and the outside of the erythrocytes. Hypotonic dialysis is preferred.

The suspension of erythrocytes encapsulating the PLP enzyme, e.g. methioninase, and optionally PLP and/or a PLP precursor, is notably able to be obtained with the following method:
1—suspending a pellet of erythrocytes in an isotonic solution at a hematocrit level equal to or greater than 65%, cooling between +1 and +8° C.,
2—a lysis procedure, at a temperature maintained between +1 and +8° C., comprising the passing of the suspension of erythrocytes at a hematocrit level equal or greater than 65% and of a cooled hypotonic lysis solution between +1 and +8° C., into a dialysis device, such as a coil or a dialysis cartridge (the cartridge is preferred);
3—an encapsulation procedure by adding, preferably gradually, the active ingredient(s) to be encapsulated (notably in a solution made up beforehand) into the suspension before or during lysis, at a temperature maintained between +1 and +8° C.; and
4—a resealing procedure conducted in the presence of an isotonic or hypertonic, advantageously hypertonic solution, at a higher temperature, notably comprised between +30 and +42° C.

In a preferred alternative, inspiration may be drawn from the method described in WO-A-2006/016247 (EP 1 773 452):
  1—suspending a pellet of erythrocytes in an isotonic solution at a hematocrit level equal to or greater than 65%, cooling between +1 and +8° C.,
  2—measuring osmotic fragility from a sample of erythrocytes from this same pellet,
  3—a lysis procedure, at a temperature maintained between +1 and +8° C., comprising the passing of the suspension of erythrocytes at a hematocrit level equal to or greater than 65% and of a hypotonic lysis solution cooled between +1 and +8° C., into a dialysis device, such as a coil or a dialysis cartridge (the cartridge is preferred); the lysis parameters being adjusted according to the osmotic fragility measured earlier; notably, depending on the measured osmotic fragility, the flow of the erythrocyte suspension passing into the dialysis device is adjusted or the osmolarity of the lysis solution is adjusted; and
  4—a procedure for encapsulation by adding, preferably gradually, the active ingredient(s) to be encapsulated (notably in a solution made beforehand) in the suspension before and during lysis, at a temperature maintained between +1 and +8° C.; and
  5—a resealing procedure conducted in the presence of an isotonic or hypertonic, advantageously hypertonic solution, at a higher temperature, notably comprised between +30 and +42° C.

Notably, for dialysis, the pellet of erythrocytes is suspended in an isotonic solution with a high hematocrit level, equal to or greater than 65%, and preferably equal to or greater than 70%, and this suspension is cooled between +1 and +8° C., preferably between +2 and +6° C., typically around +4° C. According to a particular method, the hematocrit level is comprised between 65 and 80%, preferably between 70 and 80%.

When it is measured, the osmotic fragility is advantageously measured on erythrocytes just before the lysis step, in the presence or in the absence, preferably in the presence of the active ingredient(s) to be encapsulated. The erythrocytes or the suspension containing them are advantageously at a temperature close to, or identical with the temperature selected for lysis. According to another advantageous feature of the invention, the conducted measurement of the osmotic fragility is rapidly utilized, i.e. the lysis procedure is carried out in a short time after taking the sample. Preferably, this lapse of time between the sampling and beginning of lysis is less than or equal to 30 minutes, still better less than or equal to 25 and even to 20 minutes.

As regards to how to conduct the lysis-resealing procedure with measurement and taking into account of the osmotic fragility, one skilled in the art may refer for more details to WO-A-2006/016247. This document is incorporated herein by reference.

An enhancement of the encapsulation techniques was described in FR 1 354 204 filed on May 7, 2013, to which one skilled in the art may refer and which is incorporated herein by reference. Thus, according to an embodiment, the erythrocytes encapsulating the active ingredients, i.e. the PLP enzyme, e.g. methioninase, and optionally one or several other active ingredients such as PLP and/or a PLP precursor, are obtained by a method comprising the encapsulation of the active ingredient inside erythrocytes by lysis-resealing, the obtaining of a suspension or of a pellet comprising erythrocytes incorporating the active ingredient and a solution with an osmolality greater than or equal to 280 mOsmol/kg, in particular between about 280 and about 380 mOsmol/kg, preferably between about 290 and about 330 mOsmol/kg, the incubation of the pellet or of the suspension as such or after adding an incubation solution, at an osmolality greater than or equal to 280 mOsmol/kg, in particular between about 280 and about 380 mOsmol/kg, preferably between about 290 and about 330 mOsmol/kg. Incubation is notably carried out for a period greater than or equal to 30 minutes, in particular greater than or equal to 1 h. It is then proceeded with removal of the liquid medium of the incubated solution and the erythrocytes obtained are suspended in a solution allowing injection of the suspension into a patient, preferably a preservation solution allowing injection of the suspension into a patient. The indicated osmolality is that of the solution in which the erythrocytes are suspended or in a pellet at the relevant moment.

According to a particular method, a non-phosphate PLP precursor, notably a non-phosphate form of vitamin B6 is provided during the production or storage method or in the final formulation. This compound may for example be incorporated into the incubation solution or into the preservation solution, or further into the formulation before injection when a pre-injection dilution is carried out.

According to a feature, notably 0.1 to 250, preferably from 1 to 50 mM of PN and/or of PL and/or of PM are provided during the production or storage method or in the final formulation. As described above, a fraction of these non-phosphate derivatives of vitamin B6 will be converted into PLP in the red blood cells.

By <<stabilized erythrocyte suspension>>, is notably meant a suspension having an extracellular hemoglobin content which remains less than or equal to 0.2 g/dl until its use in humans, the latter may intervene notably from 1 to 72 hours after producing the erythrocyte batch incorporating the active ingredient.

By <<ready-to-use stabilized erythrocyte suspension>>, is meant the stabilized suspension in a solution allowing injection into a patient, notably in a preservation solution. Its hematocrit is generally equal to or greater than 35%, 40% or 45%.

By <<erythrocyte pellet>>, is meant a concentrate or concentration of erythrocytes collected after separating the erythrocytes of the liquid medium in which they were suspended previously. The separation may be ensured by filtration or by centrifugation. Centrifugation is the means generally used for such a separation. A pellet comprises a certain proportion of liquid medium. Generally, the pellet has a hematocrit comprised between 70 and 85%.

By <<incubation solution>>, is meant the solution in which the erythrocytes encapsulating an active ingredient are present during the incubation step. The incubation may be accomplished over a large range of hematocrits, notably between 10 and 85% of hematocrit.

By <<fragile erythrocytes>>, are meant the erythrocytes stemming from the incorporation procedure which may, once suspended in a preservation solution, be lyzed when the suspension is preserved between 2 and 8° C., notably after 1 to 72 h.

By <<initial hematocrit>>, is meant the hematocrit before cell loss due to lysis of the fragile erythrocytes during incubation.

The method may notably comprise the following steps:
(a) encapsulation of the active ingredient(s) to be encapsulated (PLP enzyme, e.g. methioninase, and optionally PLP and/or a PLP precursor) inside erythrocytes, comprising the putting of the erythrocytes into contact with a hypotonic medium (allowing opening of pores in the membrane of the erythrocytes), the contacting with the active ingredient (for allowing it to enter the erythrocytes), the resealing of the erythrocytes, notably by means of an isotonic or hypertonic medium, advantageously hypertonic,
(b) obtaining or preparing a suspension or pellet comprising erythrocytes incorporating the active ingredient and a solution with an osmolality greater than or equal to 280 mOsmol/kg, in particular between about 280 and about 380 mOsmol/kg, preferably between about 290 and about 330 mOsmol/kg,
(c) incubating the pellet or the suspension of step (b) as such or after adding an incubation solution, at an osmolality greater than or equal to 280 mOsmol/kg, in particular between about 280 and about 380 mOsmol/kg, preferably between about 290 and about 330 mOsmol/kg, for a period greater than or equal to 30 minutes, notably greater than or equal to 1 h,
(d) removing the liquid medium of the incubated suspension of step (c),
(e) suspending the erythrocytes obtained under (d) into a solution allowing injection of the suspension into a patient, preferably a preservation solution allowing injection of the suspension into a patient.

The vitamin B6 in the non-phosphate form may be added during the encapsulation step, in step (a) or during the incubation in step (c) or further in the preservation solution.

According to a first method, the step following the encapsulation by lysis-resealing, notably step (b), includes at least 1 washing cycle, preferably 2 or 3 washing cycles, by dilution of the obtained suspension or pellet in the lysis-resealing step or step (a) in a solution, at an osmolality greater than equal to 280 mOsmol/kg, in particular between about 280 and about 380 mOsmol/kg, preferably between about 290 and about 330 mOsmol/kg, and then obtaining a pellet of erythrocytes or a suspension. This pellet or this suspension comprises erythrocytes incorporating the active ingredient and a solution with an osmolality greater than or equal to 280 mOsmol/kg, in particular between about 280 and about 380 mOsmol/kg, preferably between about 290 and about 330 mOsmol/kg. The following steps, e.g. (c), (d) and (e) are then applied.

According to a second method, in the lysis-resealing step or step (a), resealing of the erythrocytes by means of an isotonic or hypertonic medium produces the suspension of erythrocytes which may then be subject to incubation, e.g. the suspension of step (b), in a solution with an osmolality greater than or equal to 280 mOsmol/kg, in particular between about 280 and about 380 mOsmol/kg, preferably between about 290 and about 330 mOsmol/kg. In other words, the lysis-resealing step or step (a) includes a step for resealing the erythrocytes wherein the suspended erythrocytes encapsulating an active ingredient are mixed with an isotonic or hypertonic resealing solution, advantageously hypertonic, producing a suspension of erythrocytes with an osmolality greater than or equal to 280 mOsmol/kg, in particular between about 280 and about 380 mOsmol/kg, preferably between about 290 and about 330 mOsmol/kg. In this method, the incubation step or step (c) comprises incubation of the suspension stemming from the resealing. The incubation is carried out for a period greater than or equal to 30 minutes, notably greater than or equal to 1 h. The following steps, e.g. (d) and (e) are then applied.

The steps following the lysis-resealing, e.g. (b) to (e), are conducted under conditions resulting in the lysis of fragile erythrocytes, or of a majority of them, notably more than 50, 60, 70, 80 or 90%, or more. To do this, it is possible to act on the incubation period, the incubation temperature and on the osmolality of the solution in which the erythrocytes are suspended. The higher the osmolality, the longer the incubation time may be. Thus the lower the osmolality, the shorter may be the incubation in order to obtain the same effect. Also, the higher the temperature, the shorter the incubation time may be, and vice versa. One or several washing cycles will then allow removal of cell debris and extracellular hemoglobin, as well as the extracellular active ingredient.

According to the invention, a washing cycle comprises the dilution of the suspension or pellet of erythrocytes, and then the separation between the erythrocytes and the washing solution. Preferably, a washing step comprises preferably 2 or 3 dilution-separation cycles. The separation may be achieved by any suitable means, such as filtration and centrifugation. Centrifugation is preferred.

Incubation is not limited by the hematocrit of the suspension. In this way, a suspension having an initial hematocrit generally comprised between 10 and 85%, notably between 40 and 80% may be incubated. This is rather referred to as a pellet from 70% and as a suspension below this value.

The removal step or step (d) aims at removing the liquid portion of the suspension or of the incubated pellet, in order to notably remove cell debris and the extracellular hemoglobin, as well as consequently the extracellular active ingredient.

According to a first method for the removal step or step (d), separation, notably centrifugation is carried out, this being notably applicable to a suspension. This separation may be followed by one or several, for example 2 or 3, washing cycles, by dilution in an isotonic solution, and then separation, notably by centrifugation.

According to a second method for the removal step or step (d), dilution before separation notably centrifugation is carried out, this being applicable to a suspension or to a pellet. The dilution may notably be carried out with an isotonic washing solution or with a preservation solution.

The final step or step (e) consists of preparing the final suspension such that it may be administered to the patient, without any other treatment.

According to a first method for this step, a dilution of the erythrocyte pellet from the removal step or step (d) is carried out with the injection solution, notably the preservation solution.

According to a second method for this step, one or several cycles for washing the erythrocyte pellet stemming from the removal step or step (d) is carried out with the injection solution, notably the preservation solution, by dilution followed by separation. After washing, the erythrocytes are re-suspended in the injection solution, notably the preservation solution.

The method of the invention may further comprise one, several or the totality of the following features:
- the incubation step or step (c) is carried out at a temperature comprised between about 2 and about 39° C., over sufficient time for ensuring lysis of fragile erythrocytes;
- the incubation step or step (c) is carried out at a low temperature, notably comprised between about 2 and about 10° C., in particular between about 2 and about 8° C., and lasts for about 1 h to about 72 h, notably from about 6 h to about 48 h, preferably from about 19 h to about 30 h;
- the incubation step or step (c) is conducted at a higher temperature comprised between about 20 and about 39° C., notably at room temperature (25° C.±5° C.) and lasts for about 30 min to about 10 h, notably from about 1 h to about 6 h, preferably from about 2 h to about 4 h; it is possible to operate at an even higher temperature than room temperature, but this may have a negative impact on the cell yield, P50 and/or the 2,3-DPG content;
- in the incubation step or step (c), the suspension is at an initial hematocrit comprised between 10 and 85%, notably between 40 and 80%; a pellet from separation, having for example a hematocrit between 70 and about 85%, or a diluted pellet having a hematocrit comprised between about 40 and 70% may be incubated;
- the incubation step comprises stirring of the suspension;
- the incubation step does not comprise any stirring;
- as a solution for washing and/or incubation, a metered aqueous NaCl solution is used for obtaining the desired osmolality; as an example, a solution may thus comprise 0.9% of NaCl; this solution may also comprise, notably in addition to NaCl, glucose, notably glucose monohydrate, monosodium phosphate dihydrate, disodium phosphate dodecahydrate; as an example, a composition comprises: 0.9% of NaCl, 0.2% of glucose monohydrate, 0.034% of monosodium phosphate dihydrate, 0.2% of disodium phosphate dodecahydrate;
- the washing in the final step or step (e) is carried out with the preservation solution;
- the osmolality of the solution (liquid portion) in the ready-to-use suspension or which may be injected into the patient is comprised between about 280 and about 380 mOsmol/kg, preferably between about 290 and about 330 mOsmol/kg;
- the hematocrit of the ready-to-use suspension or which may be injected into the patient is equal to or greater than 35%, 40% or 45%;
- all the steps for washing, incubation are carried out with the preservation solution;
- the washing solution of step (b) and/or the washing solution of step (e) and the preservation solution are of the same composition and comprise compound(s) promoting preservation of the erythrocytes;
- the preservation solution (and the washing solution(s) or the incubation solutions if necessary) is an aqueous solution comprising NaCl, adenine and at least one compound from among glucose, dextrose and mannitol;
- the preservation solution (and the washing or incubation solution(s) if necessary) comprises NaCl, adenine and dextrose, preferably an AS3 medium;

the preservation solution (and the washing or incubation solution(s), if necessary) comprise NaCl, adenine, glucose and mannitol, preferably a SAG-Mannitol or ADsol medium.

The methods according to the invention notably comprise the following step:

(a) encapsulating an active ingredient inside erythrocytes, comprising the contacting with a hypotonic medium allowing opening of pores in the membrane of the erythrocytes, the contacting with the active ingredient in order to allow its entry into the erythrocytes, the resealing of the erythrocytes by means of an isotonic or hypertonic medium. It should be noted that the active ingredient may be present in the suspension of erythrocytes before the lysis of the latter, or further be added during lysis or after lysis, but always before resealing. In an embodiment of this step (a), the method comprises the following sub-steps:

(a1) having a suspension of erythrocytes at a hematocrit equal to or greater than 60 or 65%, (a2) measuring the osmotic fragility of the erythrocytes in this suspension, (a3) a procedure for lysis and internalization of the active ingredient(s), comprising the passing of the erythrocyte suspension into a dialysis device, notably a dialysis cartridge, counter to a lysis solution, adjusting the flow of the erythrocyte suspension or adjusting the flow rate of the lysis solution or adjusting the osmolarity of the lysis solution, depending on the osmotic fragility measured under (a2), (a4) a procedure for resealing the erythrocytes.

Another object of the invention is a therapeutic treatment method intended to provide a patient in need thereof, with a PLP enzyme and its cofactor, under conditions of good bioavailability, which means that the enzyme and its cofactor are available for each other and in an effective amount so that the enzyme is active and efficient in a therapeutic application. This method notably aims at depleting or reducing the plasmatic or circulating concentration and/or the concentration at an organ, of a substrate of the enzyme. This method comprises the administration of an effective amount of a composition according to the invention or the use of a kit according to the invention.

According to a first sub-object, the invention is a therapeutic treatment method allowing depletion or reduction of plasmatic or circulating methionine in a patient in need thereof. This method comprises the administration of an effective amount of a composition according to the invention or the use of a kit according to the invention, comprising methioninase and its cofactor. The method is a method for treating cancer, notably a cancer comprising tumoral cells auxotrophic for methionine, notably breast, lung, colon, kidney, bladder, melanoma and glioblastoma cancers.

According to a second sub-object, the invention is a therapeutic treatment method allowing depletion or reduction in plasmatic or circulating or hepatic homocysteine in a patient in need thereof. This method comprises the administration of an effective amount of a composition according to the invention or the use of a kit according to the invention, comprising methioninase and its cofactor. The method is a method for treating homocysteinuria and/or a hyperhomocysteinemia and/or pathologies associated with hyperhomocysteinemia, such as a cardiovascular disease, a disease of the central nervous system, a disease of the ocular system and/or a disease of the skeleton.

According to a third sub-object of the invention, the invention is a therapeutic treatment method allowing depletion or reduction in the plasmatic or circulating tyrosine in a patient in need thereof. This method comprises the administration of an effective amount of a composition according to the invention or the use of a kit according to the invention, comprising TPL and its cofactor. The method is a method for treating a cancer, notably a cancer comprising tumoral cells auxotrophic for tyrosine, notably melanomas.

According to a fourth sub-object of the invention, the invention is a therapeutic treatment method allowing depletion or reduction of the plasmatic or circulating and/or hepatic tyrosine in a patient in need thereof. This method comprises the administration of an effective amount of a composition according to the invention or the use of a kit according to the invention, comprising hTATase and its cofactor. The method is a method for treating a rare disease related to a deficiency of this PLP enzyme, notably the Richner-Hanhart syndrome (tyrosinemia of type II).

According to a fifth sub-object of the invention, the invention is a therapeutic treatment method allowing depletion or reduction in plasmatic or circulating and/or hepatic homocysteine in a patient in need thereof. This method comprises the administration of an effective amount of a composition according to the invention or the use of a kit according to the invention, comprising cystathionine beta-synthase and its cofactor. The method is a method for treating homocysteinuria and/or hyperhomocysteinemia and/or pathologies associated with hyperhomocysteinemia, such as a cardiovascular disease, a disease of the central nervous system, a disease of the ocular system and/or a disease of the skeleton.

The composition used in these therapeutic applications may further comprise the cofactor of this PLP enzyme, i.e. PLP, and/or a precursor thereof, which may be a non-phosphate precursor, such as a non-phosphate form of vitamin B6, and/or a phosphate precursor, such as pyridoxine phosphate (PNP). The composition may also comprise PN-kinase, PNP-oxidase, an agent inhibiting PLP-phosphatase. More generally the treatment method may comprise the administration of a composition or a kit as described above.

One administer to the patient per month of treatment, one or several doses, notably one or two, representing 50 to 300 ml of suspension or composition with a hematocrit greater than or equal to 35%, 40% or 45%, in one or several injections. They are notably administered by intravenous or intra-arterial injection, notably by perfusion.

Alternatively, an effective amount of a composition comprising erythrocytes encapsulating the PLP enzyme, e.g. methioninase, and an effective amount of a solution containing a non-phosphate form of vitamin B6, preferably PN are administered separately to the same patient. This non-phosphate form of vitamin B6 may be administered by injection, either simultaneously or separately with the suspension of erythrocytes or via any other route, notably an oral route.

In a first embodiment, a suspension of erythrocytes encapsulating the active ingredient(s), prepared within 1 and 72 h, notably for between 10 and 72 h before injection is injected to the patient. This suspension has a hematocrit equal to or greater than 35%, 40% or 45%. It is found in a preservation solution. The extracellular hemoglobin level is equal to or less than 0.5, in particular 0.3, notably 0.2, preferably 0.15, still better 0.1 g/dl, and/or the hemolysis level equal to or less than 2, notably 1.5, preferably 1%. The suspension is not washed or subject to a similar operation before injection.

Another object of the invention is a process for producing methioninase, under purified form, and with high yield, comprising the steps of:

(a) culturing bacteria transformed to produce methioninase, centrifugation of the culture and recovering of the pellet,
(b) suspending the pellet in a lysis buffer and lysis of the bacteria cells, centrifugation and recovery of the supernatant,
(c) treating the supernatant with a precipitating agent, precipitation and recovery of the pellet,
(d) applying to the pellet two rounds of crystallization or precipitation using PEG at a temperature comprised between about 25 and 40° C., recovering the pellet,
(e) suspending the pellet in a solubilization buffer (for example [25 mM Tris; 0.5 mM P5P; 0.5 mg/mL beta mercapto ethanol; pH 7.5]) and subjecting to two rounds of anion exchange chromatography, recovering a solution of methioninase,
(f) submitting the solution of methioninase to a polishing step by chromatography, recovery of a purified methioninase solution.

In a preferred embodiment, use is made of the methioninase coding sequence of *Pseudomas putida*. This sequence may be optimized in order to adapt the sequence to the production strain. The production strain is preferably *E. coli*, such as strain HMS174. An expression vector containing the methioninase sequence, preferably the optimized one, is used to transform the producing strain, and a producing clone may be selected. Then production of methioninase using this clone is performed in a fermenter under usual conditions.

Preferably, the pellet of step (a) is resuspended in the lysis buffer (for example [100 mM Sodium phosphate; 4.4 mM EDTA; 3.3 mM P5P; 1 mM DTT; pH 7.6]) (7 mL per gram of wet weight). Preferably, lysis is made by high pressure homogenization, advantageously in several steps, preferably 3 steps of high pressure homogenization. Typical temperature is maintained about 10° C. before each step of homogenization (between 9 to 12° C.). Preferably, after lysis and before centrifugation, the cell lysate is submitted to clarifying using a cationic coagulant, preferably polyethyleneimine (PEI). Typical PEI concentration may be between about 0.05 and about 0.5% (V/V), in particular between about 0.1 and about 0.3% preferably about 0.2%.

Precipitation at step (c) may be performed with ammonium sulfate, typically at about 60% saturation. Preferably, before this precipitation, the supernatant is filtered on an about 0.2 µm membrane.

At step (d), PEG is preferably PEG-6000. Its final concentration may be between about 5 and about 25% (W/V), in particular between about 5 and about 15%. The first round may preferably be performed in the presence of ammonium sulfate. Typically, ammonium sulfate may be at about 10% saturation (between 9 to 11%). Typically, PEG may be at about 10% final concentration. The second round may preferably be performed in the presence of an inorganic salt, typically an alkaline metal salt such as sodium chloride or potassium chloride, preferably sodium chloride. The salt may be at a final concentration of about 0.20 M (between 0.19 and 0.21). Typically, PEG may be at about 12% final concentration. Temperature may be comprised between about 25 and about 35° C., in particular between about 28 and about 32° C., typically about 30° C.

At step (e) chromatography may be performed on DEAE sepharose. Preferably, before chromatography, the resuspended pellet or sediment may be submitted to passage through an about 0.45 µm filter.

At step (f), polishing is performed to remove remaining residual contaminants such as endotoxins, HCP and DNA. It may be performed using a Q membrane chromatography.

The purified methioninase may then be concentrated and diafiltered. Conservation may be made through freeze-drying and storage at about −80° C. The invention will now be described in more detail by means of embodiments taken as non-limiting examples and with reference to the drawing wherein:

FIG. 1: Description of the method for purifying MGL, according to the method described in EP 0 978 560 and according to the improved method described in the present application. The modifications brought to the method described in patent EP 0 978 560 B1 relate to the steps located after the precipitation step with ammonium sulfate.

Figure 2:
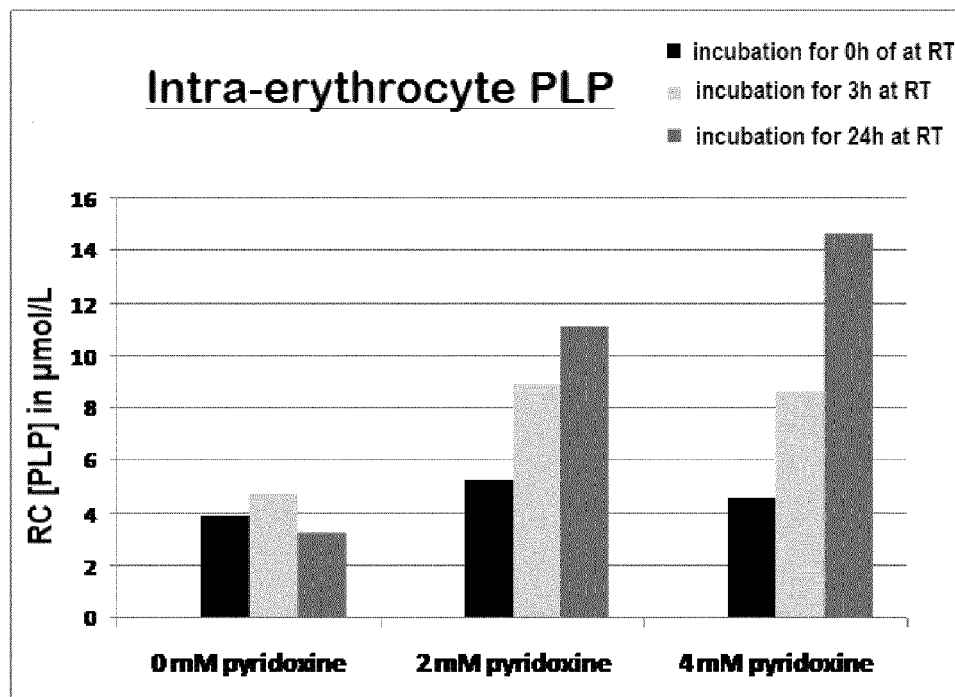
Figure 3:
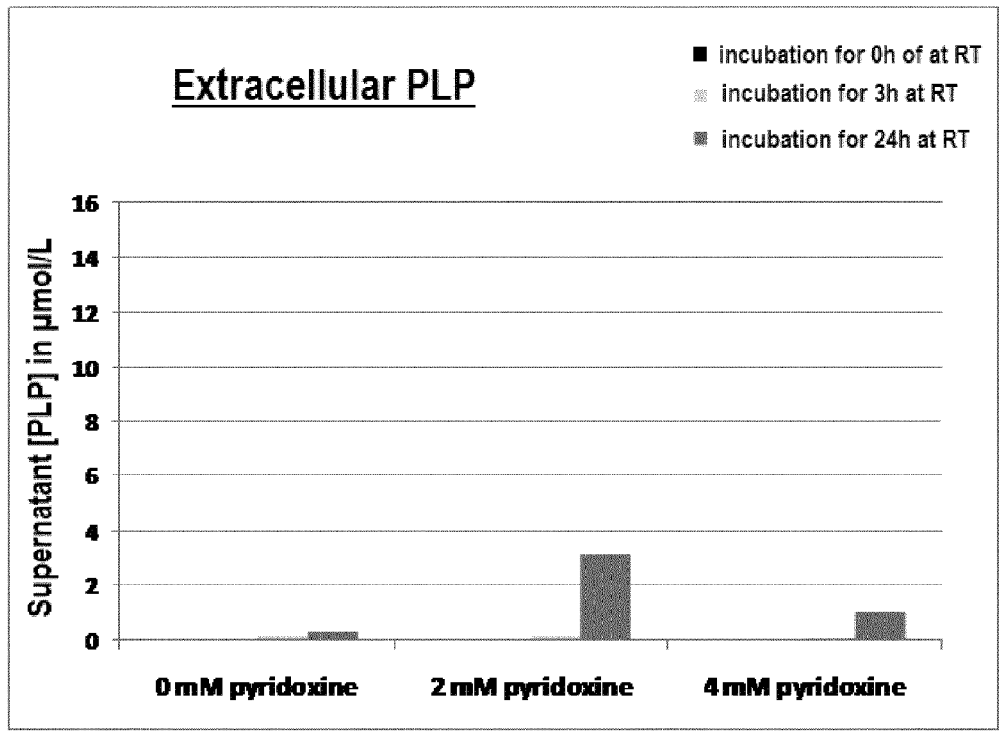

FIGS. 2 and 3. Comparison of the intra-erythrocyte concentrations (FIG. 2) and extracellular concentrations (FIG. 3) of PLP after incubation of a RC-MGL-PLP suspension with pyridoxine (PN) at different concentrations. The RC-MGL-PLP suspension, incubated for 3 h and 24 h at room temperature in the absence of pyridoxine (0 mM) has a basal PLP level of about 3.9 µM. The incubation of the suspensions with 2 mM and 4 mM pyridoxine gives the possibility of increasing the intra-erythrocyte PLP concentration to 8 µM after 3 h of incubation (pale grey bars) and gives the possibility of attaining considerably higher levels (11 µM and 14 µM respectively) after 24 h of incubation (dark grey bars).

Figure 4:
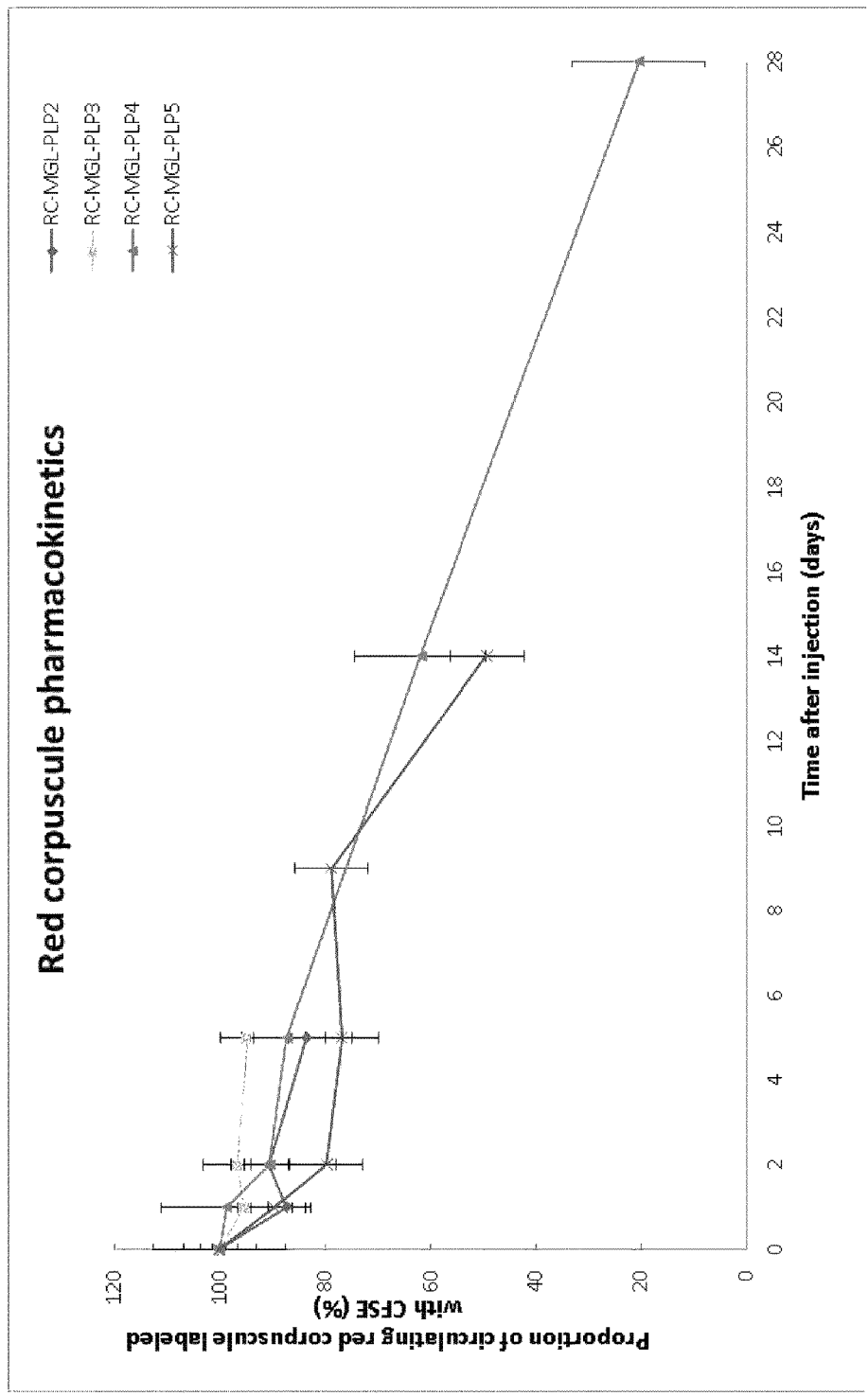

FIG. 4. Pharmacokinetics of red corpuscles (RCs) loaded with a complex MGL-PLP. The RC-MGL-PLP2 product is obtained by lysis-resealing of a suspension containing 3 mg/ml of MGL and ~30 µM of PLP. The RC-MGL-PLP3 product is obtained by lysis-resealing of a suspension containing 3 mg/ml of MGL and ~125 µM of PLP. The RC-MGL-PLP4 product is obtained by lysis-resealing of a suspension containing 5 mg/ml of MGL and 33 µM of PLP. The RC-MGL-PLP5 product is obtained by lysis-resealing of a suspension containing 6 mg/ml of MGL and 100 µM of PLP. Fluorescent labeling of the products (CFSE) allows traceability of the RCs in vivo. The products injected intravenously to the mice CD1 (8 ml/kg for the products RC-MGL-PLP2, RC-MGL-PLP3 and RC-MGL-PLP5 and 10 ml/kg for the product RC-MGL-PLP4) have excellent stability with a survival rate of the injected RCs greater than 75% at 120 h, i.e. 5 days after their administration. For the RC-MGL-PLP4 product, the survival rate is reduced to less than 75% after ~10 days.

Figure 5:
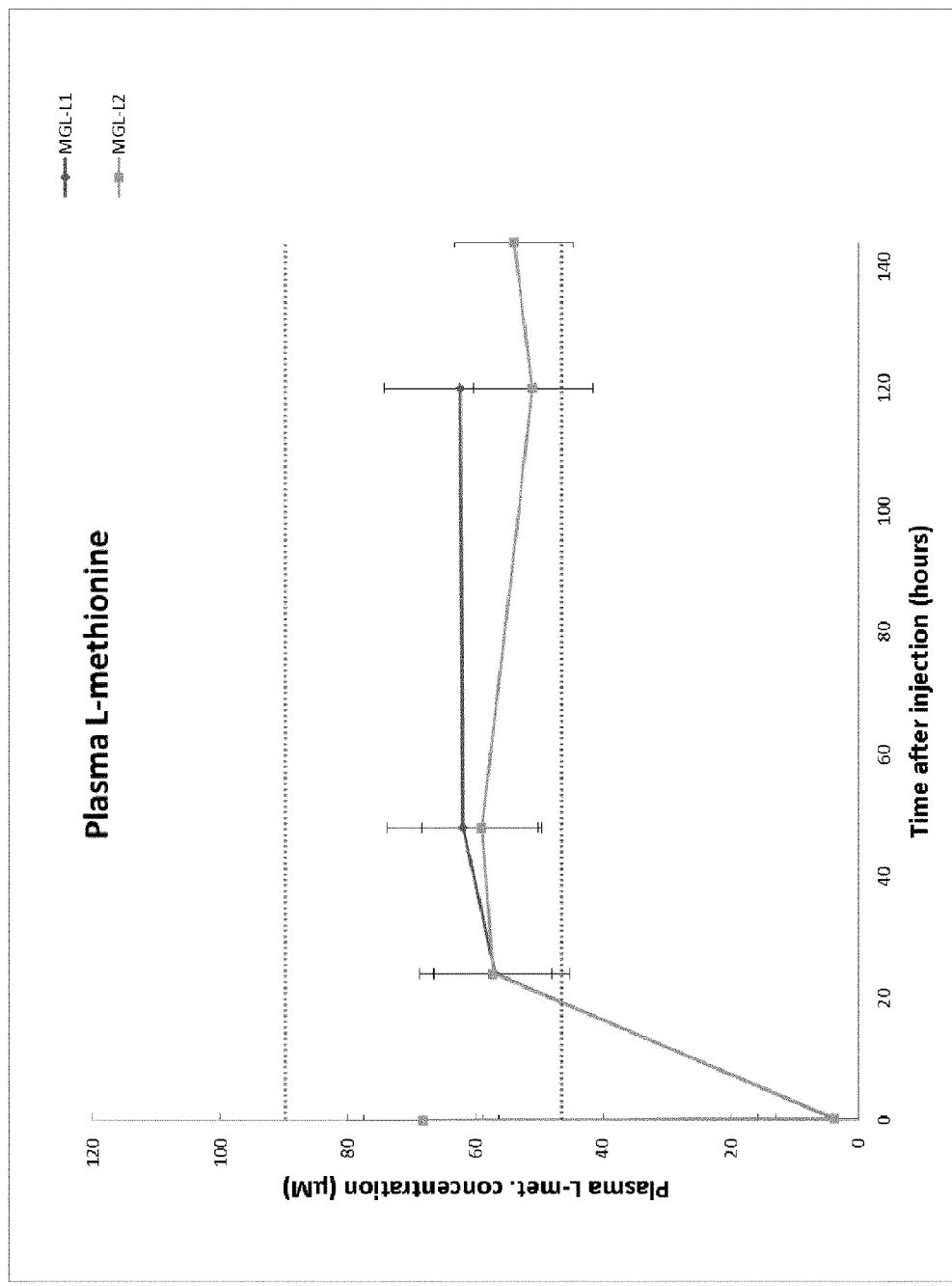

FIG. 5. Pharmacodynamics of the free MGL enzyme. The MGL enzyme was diluted by means of a potassium phosphate solution supplemented with 10 µM of P5P in order to obtain two injectable products (MGL-L1 and MGL-L2). These products were made so as to obtain 1) the same enzyme concentration as the product RC-MGL-PLP2, i.e. 0.45 mg/ml of MGL and 2) a concentration twice greater than the product RC-MGL-PLP2, i.e. 0.90 mg/ml of MGL. Both products are administered intravenously (IV) to CD1 mice (8 ml/kg) with supplementation IV of pyridoxine 6 h after the injection. The plasma L-methionine level is measured by HPLC-MS-MS. The L-Met level in non-treated CD1 was evaluated to be 68 µM. These products MGL-L1 and MGL-L2 both lead to rapid depletion within 15 min after their administration but not long lasting over time.

Figure 6:
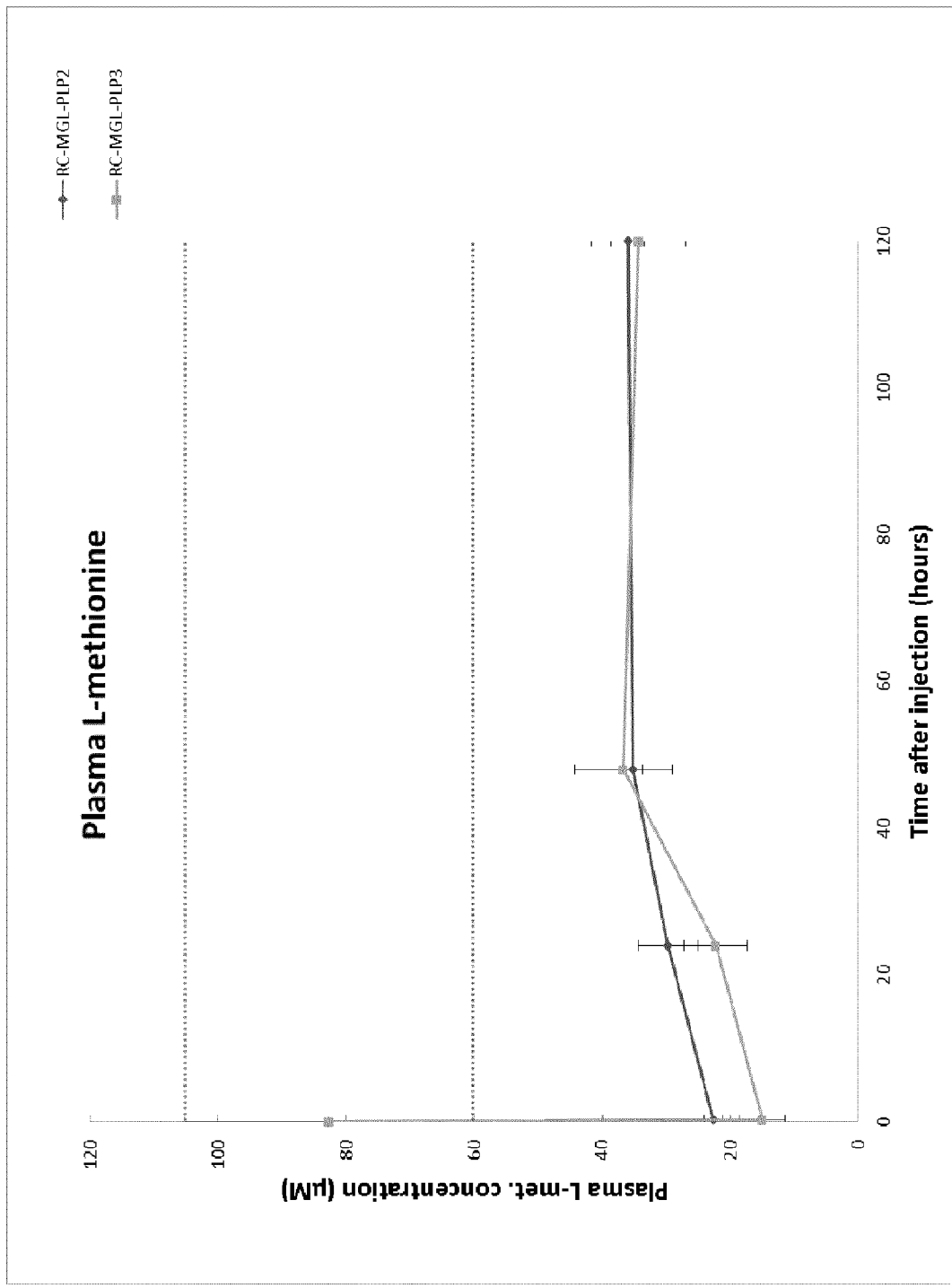

FIG. 6. Pharmacodynamics of the RC-MGL-PLPs over short times. The product RC-MGL-PLP2 is obtained by lysis-resealing of a suspension containing 3 mg/ml of MGL and ~30 µM of PLP. The product RC-MGL-PLP3 is obtained by lysis-resealing of a suspension containing 3 mg/ml of MGL and ~125 µM of PLP. Both products are administered intravenously (IV) to CD1 mice (8 ml/kg) with IV supplementation of pyridoxine 6 h after administration for the mice receiving RC-MGL-PLP2. The plasma L-methionine level is measured by HPLC-MS-MS. The L-Met level in untreated CD1s was evaluated to be 82 µM. Both products RC-MGL-PLP2 and RC-MGL-PLP3 lead to rapid depletion 15 min after their administration reducing the L-Met level to 15.0±3.6 µM and 22.7±1.5 µM respectively and then maintaining more moderate depletion at 35 µM but stable between 48 h and 120 h.

Figure 7:
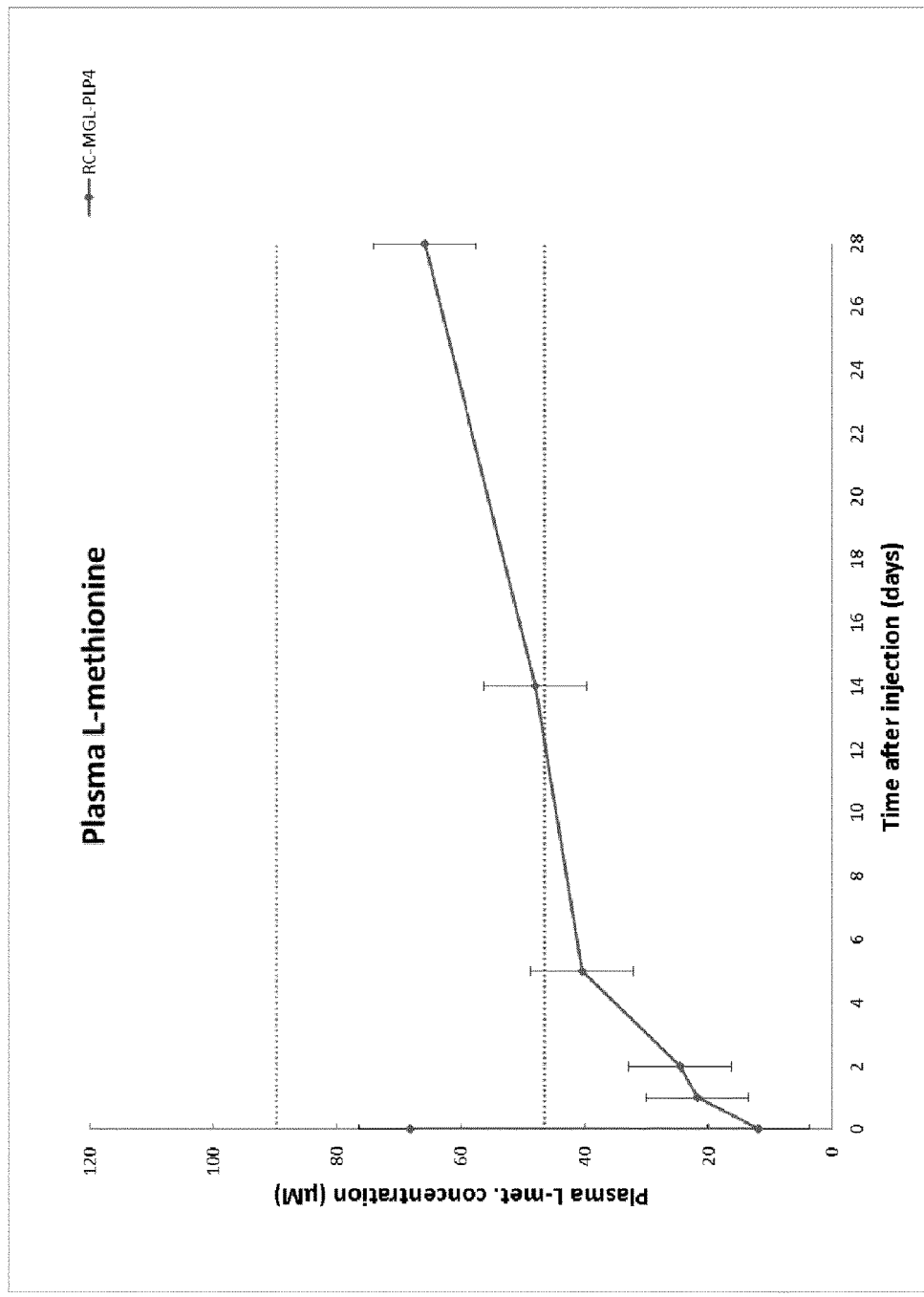

FIG. 7. Pharmacodynamics of the RC-MGL-PLPs over long periods. The product RC-MGL-PLP4 (0.5 mg/ml) is obtained by lysis-resealing of a suspension containing 5 mg/ml of MGL and 33 µM of PLP. The product is administered intravenously (IV) to CD1 mice (10 ml/kg) with IV supplementation of pyridoxine 6 h after administration for the mice receiving RC-MGL-PLP4. The plasma L-methionine level is measured by HPLC-MS-MS. The L-Met level in untreated CD1s was evaluated to be 68 µM. The product RC-MGL-PLP4 leads to rapid depletion 15 min after administration reducing the L-Met level to ~10 µM and then maintaining more moderate depletion at ~25 µM but stable between 24 h and 48 h so as to then gradually return to the control values 12 days after injection.

Figure 8:
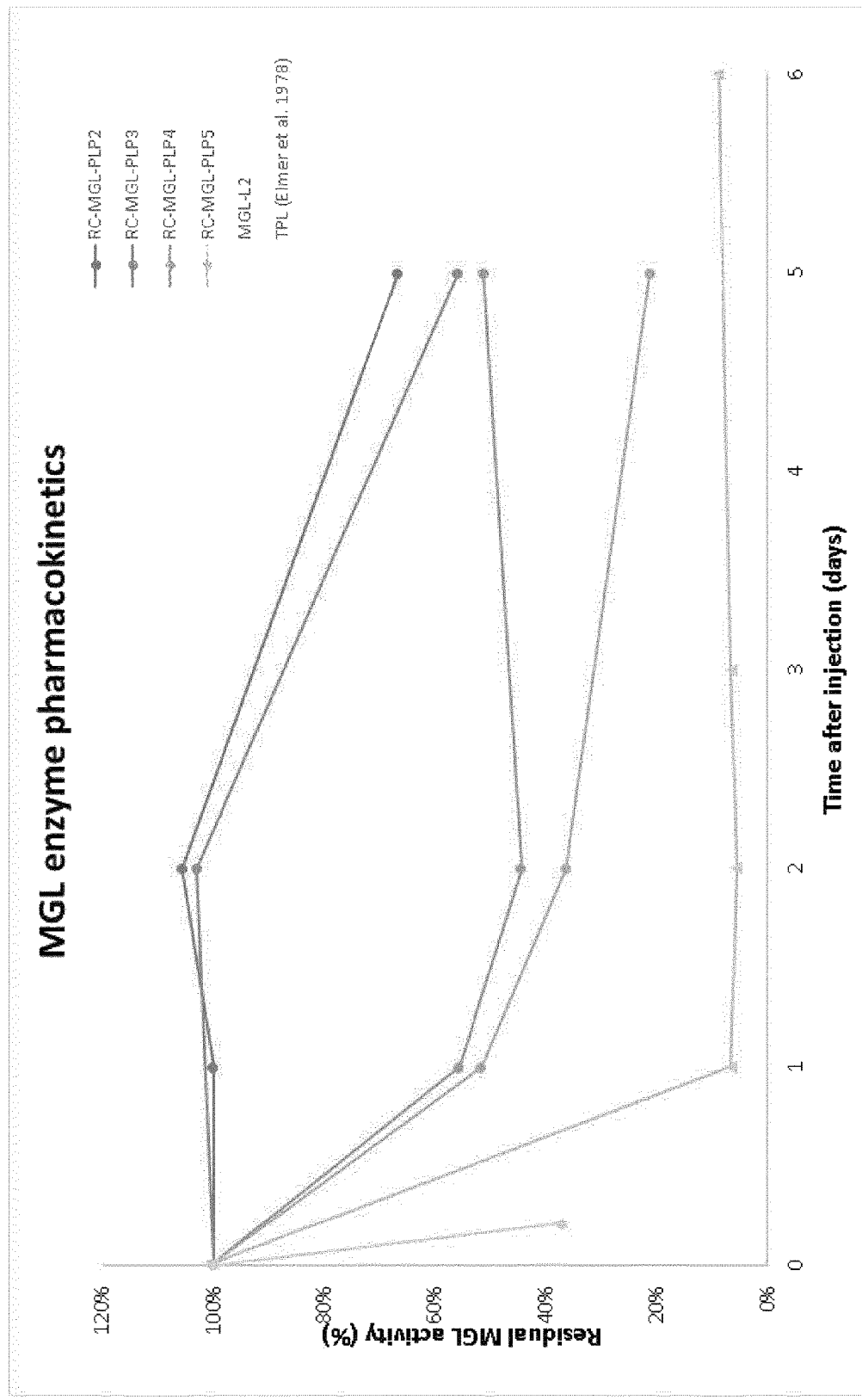

FIG. 8. Residual activity of circulating PLP enzymes. The enzyme MGL was diluted by means of a potassium phosphate solution supplemented with 10 µM of P5P in order to obtain the injectable product MGL-L2. The product RC-MGL-PLP2 is obtained by lysis-resealing of a suspension containing 3 mg/ml of MGL and ~30 µM of PLP. The product RC-MGL-PLP3 is obtained by lysis-resealing of a suspension containing 3 mg/ml of MGL and ~125 µM of PLP. The product RC-MGL-PLP4 is obtained by lysis-resealing of a suspension containing 5 mg/ml of MGL and 33 µM of PLP. The product RC-MGL-PLP5 is obtained by lysis-resealing of a suspension containing 6 mg/ml of MGL and 100 µM of PLP. The products are injected intravenously to CD1 mice (8 ml/kg for the products MGL-L2, RC-MGL-PLP2, RC-MGL-PLP3 and RC-MGL-PLP5 and 10 ml/kg for the product RC-MGL-PLP4). The residual activity of the injected MGL enzyme (total RCs) is determined by a measurement of the $NH_3$ produced by MGL according to the method described in Example 4.

EXAMPLE 1

Method for Obtaining and Characterizing Methionine Gamma Lyase (MGL)

Production of the strain and isolation of a hyper-producing clone: the natural sequence of MGL of *Pseudomonas putida* (GenBank: D88554.1) was optimized by modifying rare codons (in order to adapt the sequence stemming from *P. putida* to the production strain *Escherichia coil*). Other changes have been made to improve the context of translation initiation. Finally, silent mutations were performed to remove three elements that are part of a putative bacterial promoter in the coding sequence (box −35, box −10 and a binding site of a transcription factor in position 56). The production strain *E. coli* HMS174 (DE3) was transformed with the expression vector pGTPc502_MGL (promoter T7) containing the optimized sequence and a producing clone was selected. The producing clone is pre-cultivated in a GY medium+0.5% glucose+kanamycin for 6-8 h (pre-culture 1) and 16 h (pre-culture 2) at 37° C.

Fermentation: the production is then achieved in a fermenter with GY medium, with stirring, controlled pressure and pH from the pre-culture 2 at an optical density of 0.02. The growth phase (at 37° C.) takes place until an optical density of 10 is obtained and the expression induction is achieved at 28° C. by adding 1 mM IPTG into the culture medium. the cell sediment is harvested 20 h after induction in two phases: the cell broth is concentrated 5-10 times after passing over a 500 kDa hollow fiber and then cell pellet is recovered by centrifugation at 15900×g and then stored at −20° C.

Purification: The cell pellet is thawed and suspended in lysis buffer (7 v/w). Lysis is performed at 10° C. in three steps by high pressure homogenization (one step at 1000 bars, and then two steps at 600 bars). The cell lysate then undergoes clarification at 10° C. by adding 0.2% PEI and centrifugation at 15900×g. The soluble fraction is then sterilized by 0.2 µm before precipitation with ammonium sulfate (60% saturation) at 6° C., over 20 h. Two crystallization steps are carried out on the re-solubilized sediment using solubilization buffer, the first crystallization step is realized by addition of PEG-6000 at 10% (final concentration) and ammonium sulfate at 10% saturation, and the second crystallization is then performed by addition of PEG-6000 at 12% final concentration and 0.2 M NaCl (final concentration) at 30° C. The pellets containing the MGL protein are harvested at each stage after centrifugation at 15900×g. The pellet containing the MGL protein is re-suspended in a solubilization buffer and passed over a 0.45 µm filter before being subject to two anion exchange chromatographies (DEAE sepharose FF). The purified protein is then subject to a polishing step and passed over a Q membrane chromatography capsule for removing the different contaminants (endotoxins, HCP host cell protein, residual DNA). Finally, the purified MGL protein is concentrated at 40 mg/ml and diafiltered in formulation buffer using a 10 kDa cut-off tangential flow filtration cassette. Substance is then aliquoted at ~50 mg of protein per vial, eventually freeze-dried under controlled pressure and temperature, and stored at −80° C.

Characterization: The specific activity of the enzyme is determined by measuring the produced $NH_3$ as described in example 4. The purity is determined by SDS-PAGE. The PLP level after being taken up in water was evaluated according to the method described in example 5. The osmolarity is measured with an osmometer (Micro-Osmometer Loser Type 15).

The following table summarizes the main characteristics of one produced batch of MGL:

|  | MGL of *P. putida* |
| --- | --- |
| Formulation | Freeze-dried (amount per tube: 49.2 mg). Characteristics after being taken up in 625 µL of water: 78.7 mg/ml, ~622 µM of PLP, 50 mM of Na phosphate, pH 7.2, Osmolarity 300 mOsmol/kg. |
| Specific activity | 13.2 IU/mg |
| Purity | >98% |

Discussion of the production method. The method for purifying the MGL described in Example 1 is established on the basis of the method detailed in patent EP 0 978 560 B1 and of the associated publication (Takakura et al., Appl Microbiol Biotechnol 2006). This selection is explained by the simplicity and the robustness of the crystallization step which is described as being particularly practical and easily adaptable to large scale productions according to the authors. This step is based on the use of PEG6000 and of ammonium sulfate after heating the MGL solution obtained after the lysis/clarification and removal of impurities by adding PEG6000/ammonium sulfate steps. The other notable point of this step is the possibility of rapidly obtaining a high purity level during the step for removing the impurities by achieving centrifugation following the treatment of the MGL solution with PEG6000. The impurities are again found in the centrifugation pellet, the MGL being in majority found in solution in the supernatant. Because of this purity, the passing of the MGL solution in a single chromatography step over an anion exchanger column (DEAE), associated with a purification step by gel filtration on a sephacryl S200 HR column, gives the possibility of obtaining a purified protein.

Upon setting into place the patented method for small scale tests, it appeared that the obtained results were not able to be reproduced. According to patent EP 0 978 560 B1, at the end of the step for removing the impurities (treatment with PEG6000/ammonium sulfate and centrifugation), the MGL enzyme is in majority found in the soluble fraction, centrifugation causing removal of the impurities in the pellet. During small scale tests conducted according to the described method in EP 0 978 560 B1, the MGL protein is again in majority found (~80%) in the centrifugation pellet. The table below lists the percentage of MGL evaluated by densitometry on SDS-PAGE gel in soluble fractions.

| Purification | MGL percentage in the soluble fraction | Average |
|---|---|---|
| Test no. 1 | 11% | 17% |
| Test no. 2 | 23% | |

This unexpected result therefore led to optimization of the patented method by: 1) operating from the centrifugation pellet containing MGL, 2) carrying out two successive crystallization steps for improving the removal of the impurities after loading on a DEAE column, 3) optimizing chromatography on a DEAE column.

For this last step, it is found that the DEAE sepharose FF resin is finally not a sufficiently strong exchanger in the tested buffer and pH conditions. After different additional optimization tests, the selection was finally directed to 1) replacement of the phosphate buffer used in the initial method with Tris buffer pH 7.6 for improving the robustness of the method and 2) carrying out a second passage on DEAE in order to substantially improve the endotoxin level and the protein purity without any loss of MGL (0.8 EU/mg according to Takakura et al., 2006 versus 0.57 EU/mg for the modified method).

Finally, in order to obtain a method compatible with the requirements for large scale GMP production, a polishing step on a membrane Q was added in order to reduce the residual endotoxins and HCP levels. This final step of polishing avoids the implementation of the S200 gel filtration chromatography which is a difficult step to be used in production processes at an industrial scale (cost and duration of the chromatography).

The different purification steps of the method from EP 0 978 560 B1 as well as of the method of the present application are given in FIG. 1.

The following table gives the possibility of checking that the provided adaptations have led to obtaining a purification method with a yield at least equivalent to the one described in the initial method.

| Step | Patent EP 978 560 B1 | | Method of the application | |
|---|---|---|---|---|
| | Amount of enzyme (g) | Yield (%) | Amount of enzyme (g) | Yield (%) |
| Solubilised pellet before DEAE | 125 | 100 | 70 | 100 |
| Concentrated solution$ | 80 | 64 | 46 | 65 |

$post sephacryl S-200 HR (EP 978 560) or post Membrane Q (method of the invention).

EXAMPLE 2

Co-Encapsulation of MGL and PLP in Murine Erythrocytes

Whole blood of CD1 mice (Charles River) is centrifuged at 1000×g, for 10 min, at 4° C. in order to remove the plasma and buffy coat. The RCs are washed three times with 0.9% NaCl (v:v). The freeze-dried MGL is re-suspended in water at a concentration of 78.7 mg/ml and added to the erythrocyte suspension in order to obtain a final suspension with a hematocrit of 70%, containing different concentrations of MGL and of the PLP. The suspension was then loaded on a hemodialyzer at a flow rate of 120 ml/h and dialyzed against a hypotonic solution at a flow rate of 15 ml/min as a counter-current. The suspension was then resealed with a hypertonic solution and then incubated for 30 min at 37° C. After three washes in 0.9% NaCl, 0.2% glucose, the suspension was taken up in a preservation solution SAG-Mannitol supplemented with 6% BSA. The obtained products are characterized at D0 (within the 2 h following their preparation) and at D1 (i.e. after ~18 h-24 h of preservation at 2-8° C.). The hematologic characteristics are obtained with a veterinary automaton (Sysmex, PocH-100iV).

Results:

In the different studies mentioned hereafter, the MGL activity in the finished products is assayed with the method described in example 4 against an external calibration range of MGL in aqueous solution. These results, combined with explanatory studies, show that MGL activity in the finished products increases with the amount of enzyme introduced into the method and that it is easily possible to encapsulate up to 32 IU of MGL per ml of finished product while maintaining good stability.

In another study, three murine finished products RC-MGL-PLP1, RC-MGL-PLP2 and RC-MGL-PLP3 were prepared according to the following methods:

RC-MGL-PLP1: co-encapsulation of MGL and of PLP from a suspension containing 3 mg/ml of MGL and ~30 μM of PLP. The final product was taken up in SAG-Mannitol, 6% BSA supplemented with final 10 μM PLP.

RC-MGL-PLP2: co-encapsulation of MGL and of PLP from a suspension containing 3 mg/ml of MGL and ~30 μM of PLP. The finished product was taken up in SAG-Mannitol 6% BSA.

RC-MGL-PLP3: this product stems from a co-encapsulation of MGL and PLP from a suspension containing 3 mg/ml of MGL and ~124 µM of PLP. The final product was taken up in SAG-Mannitol 6% BSA.

In a third study, a murine finished product RC-MGL-PLP4 was prepared from a new batch of MGL according to the following methods:

RC-MGL-PLP4: co-encapsulation of MGL and the PLP from a suspension containing 5 mg/ml of MGL and ~35 µM of PLP. The finished product was taken up in SAG-Mannitol 6% BSA.

Finally in a fourth study, a murine product RC-MGL-PLP5 was prepared from a third batch of MGL according to the following methods:

RC-MGL-PLP5: co-encapsulation of MGL and PLP from a suspension containing 6 mg/ml of MGL and ~100 µM of PLP. The finished product was taken up in SAG-Mannitol 6% BSA.

The hematologic and biochemical characteristics of the three finished products at D0 (after their preparation) are detailed in the table below. The encapsulation yields are satisfactory and vary from 18.6% to 30.5%.

|  | J0 | J1 | J7 |
|---|---|---|---|
| Hematocrit (%) | 52.0 | 51.6 | 52.7 |
| Corpuscle volume (fl) | 91.0 | 92.0 | 88.0 |
| Corpuscle hemoglobin (g/dl) | 30.3 | 29.8 | 31.6 |
| RC concentration ($10^6$/µl) | 6.00 | 5.92 | 5.98 |
| Total hemoglobin (g/dl) | 16.4 | 16.2 | 16.6 |
| Extracellular Hb (g/dl) | 0.119 | 0.197 | 0.280 |
| Osmotic fragility (g/l) | 1.17 |  |  |
| Hemolysis (%) | 0.7% | 1.2% | 1.7% |
| Total MGL concentration (mg/ml) | 0.36 | 0.35 |  |
| MGL supernatant concentration (mg/ml) | 0.01 | 0.01 |  |
| MGL intra-erythrocyte concentration (mg/ml, 100% Ht) | 0.68 | 0.67 |  |
| Extracellular activity (%) | 1.3% | 1.4% |  |
| Intracellular activity (%) | 98.7% | 98.6% |  |
| Encapsulation yield (%) | 19.7% |  |  |

|  |  | RC-MGL-PLP1 | RC-MGL-PLP2 | RC-MGL-PLP3 | RC-MGL-PLP4 | RC-MGL-PLP5 |
|---|---|---|---|---|---|---|
| Hematological data | Hematocrit (%) | 50.0 | 49.6 | 50.0 | 50.0 | 50.0 |
|  | Corpuscle volume (fl) | 46.3 | 46.5 | 46.8 | 42.4 | 45.6 |
|  | Corpuscle hemoglobin (g/dl) | 24.7 | 24.0 | 24.2 | 27.4 | 25.1 |
|  | RC concentration ($10^6$/µl) | 6.5 | 6.9 | 6.6 | 7.2 | 6.0 |
|  | Total hemoglobin (g/dl) | 14.8 | 15.4 | 15.0 | 16.6 | 13.8 |
|  | Extracellular Hb (g/dl) | 0.1 | 0.1 | 0.1 | 0.2 | 0.05 |
| mgl | Intra-erythrocyte concentration of MGL (mg/ml of RC) | 0.97 | 0.94 | 0.79 | 1.01 | 1.36 |
|  | Intra-erythrocyte activity of MGL (IU/ml of RC)* | 12.8 | 12.4 | 8.8 | 5.0 | 8.6 |
|  | Extracellular activity (%) | 0.92% | 0.97% | 1.32% | 1.18% | 2.23% |
|  | Intracellular activity (%) | 99.08% | 99.03% | 98.68% | 98.82% | 97.77% |
|  | Encapsulation yield of MGL (%) | 18.6% | 30.5% | 22.6% | 19.4% | 22.7% |
| PLP | Intra-erythrocyte concentration of PLP (µmol/l of RC) | ND | 13.4 | 71.4 | 10.2 | ND |
|  | Intracellular PLP fraction (%) | ND | 99.5 | 98.7 | 98.1 | ND |
|  | Extracellular PLP fraction (%) | ND | 0.5 | 1.3 | 1.92 | ND |
|  | PLP encapsulation yield (%) | ND | 44.8 | 57.4 | 30.7 | ND |

*Calculated from the specific activity of each batch.

EXAMPLE 3

Production of Human RCs Encapsulating Methionine Gamma Lyase and PLP According to the Industrial Method A pouch of leukocyte-depleted human RCs (provided by the "Etablissement Français du Sang") is subject to a cycle of three washes with 0.9% NaCl (washer Cobe 2991). The freeze-dried MGL is re-suspended with 0.7% NaCl and added to the erythrocyte suspension in order to obtain a final suspension with a hematocrit of 70%, containing 3 mg/ml of MGL and ~30 µM of PLP (stemming from the formulation of MGL). The suspension is homogenized and it is proceeded with encapsulation according to the method described in EP 1 773 452. The suspension from the resealing is then incubated for 3 h at room temperature in order to remove the most fragile RCs. The suspension is washed three times with a 0.9% NaCl, 0.2% glucose solution (washer Cobe 2991) and then re-suspended with 80 ml of preservation solution (AS-3). The encapsulated MGL level is assayed like in Example 4.

EXAMPLE 4

Assay of Encapsulated MGL in the RCs

The assay of the MGL activity in cell suspensions (total RCs) and in the supernatants is based on a measurement of $NH_3$ produced by MGL. The $NH_3$ ions are assayed indirectly by enzymatic action of glutamate dehydrogenase (GLDH) according to the kit marketed by Roche Diagnostics (11877984).

Preparation of the standards: MGL standards at different concentrations were prepared in matrices (total or supernatant RCs) or in an aqueous solution.

For standards in an aqueous solution, MGL is prepared at concentrations varying from 0 to 12 µg/ml in the presence of 20 µM PLP in a phosphate buffer 100 mM at a pH of 7.2.)

For total RC matrix standards, 10 µl of RC-LR are lysed with 90 µl of a solution containing 260 µM of PLP and of MGL at concentrations varying from 0 to 100 µg/ml. The "total RC" standards are then diluted 20 times with phosphate buffer 100 mM, pH 7.2.

For supernatant matrix standards, 10 µl of supernatants of RC-LR are lysed with 50 µl of a solution containing 6.4 µM of PLP and of MGL at concentrations varying from 0 to 20 µg/ml.

Pre-treatment of the samples: the samples to be assayed (10 µl) are pre-treated in the same way as the standards (addition of PLP and identical dilutions but without addition of MGL).

Assay of MGL: 7.5 µl of standards (STD) or of samples are introduced into the wells of a UV plate. 94 µl of reagent R1 (Roche kit) and 56 µl of reagent R2 (Roche kit) containing α-ketoglutarate in a buffer solution, NADPH and GLDH are added in order to remove the endogenous $NH_3$ ions of the samples. After 10 min of incubation, 75 µl of L-methionine at 78.3 mM are introduced and the reaction mixtures are incubated for 30 min. Degradation of NADPH into $NADP^+$ is continuously tracked by measuring the optical density at 340 nm. For the standards and the samples, the value of ΔOD/min is calculated over the linear domain of the O.D. curves obtained at 340 nm. A calibration curve ΔOD/min=f (MGL concentration or activity in the standards) is then plotted. The regression parameters allow determination of the MGL concentration in the samples. This result may be expressed in mg/ml or in IU/ml (the specific MGL activity being evaluated for each batch). The intra-erythrocyte MGL level is obtained by a calculation with the following formula: $[MGL]_{intra-erythrocyte} = ([MGL]_{total} - ([MGL]_{supernatants} \times (1-hematocrit/100))/(hematocrit/100)$.

EXAMPLE 5

Assay of PLP in Blood Samples by a HPLC Method

The assay of PLP in cell suspensions (total RCs) and in the supernatants is an adaptation of the method described by Van de Kamp et al. Nutrition Research 15, 415-422, 1995. The assay is carried out with RP-HPLC (Shimadzu UFLC) with detection by fluorimetry (RF-10AXL instrument, excitation: 300 nm, emission: 400 nm). The PLP contained in the samples is extracted with trichloro-acetic acid (TCA) at a final 6%. After centrifugation (15,000×g, 10 min), the supernatants are collected and then diluted in a mobile phase A. A 50 µl sample volume is injected on a 5 µC-18 Gemini column, 250×4.6 mm (Phenomenex). The mobile phase A consists of 33 mM of monobasic potassium phosphate, of 8 mM of sodium 1-octanesulfonate supplemented with sodium bisulfite (0.5 g/l) for intensifying the signal of the PLP and of the mobile phase B, of 33 mM of monobasic potassium phosphate and of 17% (v:v) of 2-propanol. The gradient used is the mobile phase A (100%) with increasing proportions of mobile phase B: an increase from 0% to 8% of B over a period of 8 min. The flow through the column is maintained at 1 ml/min. The PLP concentration in the samples is determined with an external standard range of PLPs subject to the same TCA treatment as the samples. The retention time of PLP is ~3.4 min. The intra-erythrocyte PLP level is obtained by calculation with the following formula: $[PLP]_{intra-erythrocyte} = ([PLP]_{total} - ([PLP]_{supernatants} \times (1-hematocrit/100))/(hematocrit/100)$.

EXAMPLE 6

Increase in the PLP Level in RCs by Co-Encapsulation of PLP with MGL

Suspensions of murine RCs are subject to the method for encapsulating MGL and PLP as described in Example 2. The assay of the intracellular PLP is carried out according to the method described in Example 5.

A suspension of human RCs is subject to the method for encapsulating MGL and PLP as described in Example 3. Before the incubation step at room temperature, a portion of the human RC-MGL-PLPs is sampled in order to carry out an assay of the intracellular PLP according to the method described in Example 5.

The following table compares the physiological levels of PLP in human or murine erythrocytes with the level attained by co-encapsulation of the latter with MGL.

|  |  | Human RCs | Murine RCs |
| --- | --- | --- | --- |
| Physiological level of PLP |  | 0.11 µM (Natta & Reynolds) | ~2.4 µM* (Fonda) |
| PLP level in RC-MGL-PLP1s or RC-MGL-PLP2s | Conditions before dialysis: 3 mg/ml MGL ~30 µM PLP | ~3.90 µM | ~13.4 µM |
| PLP level in RC-MGL-PLP3s | Conditions before dialysis: 3 mg/ml MGL ~125 µM PLP |  | ~71.4 µM |

*detail of the calculation: 7.5 nmol/g Hb ~2.4 µM (by assuming a CCMH of 32 g/dl).

EXAMPLE 7

Demonstration of the Increase in the PLP Concentration in the RC-MGLs by Incubation In Vitro with Pyridoxine A suspension of human RCs is subject to the method for encapsulating MGL as described in Example 3. Before the 3 h incubation step, a portion of the RCs is sampled and separated into three for volume-volume incubation with pyridoxine at different concentrations (0 mM, 2 mM and 4 mM). After homogenization, these suspensions are incubated at room temperature (RT). After 3 h and 24 h of incubation, samples of the cell suspensions and of the supernatants (obtained after centrifugation of the suspensions at 1000×g, at 4° C., for 10 min) are prepared and frozen for a measurement of the PLP concentration by HPLC as described in Example 5.

The obtained results are shown in FIGS. 2 and 3.

In the absence of pyridoxine, the intra-erythrocyte PLP level is 3.9 µM (PLP stemming from the co-encapsulation of MGL and PLP). This PLP concentration remains constant after 3 h and 24 h of incubation. A slight decrease in the PLP concentration is observed at 24 h and is concomitant with occurrence of extracellular PLP which may be explained by hemolysis at the end of the incubation.

In the presence of pyridoxine (at 2 mM or at 4 mM), the RC-MGLs are enriched in PLP with intra-erythrocyte concentrations increased by a factor 2 after 3 h of incubation (~8 µM of PLP) and by almost a factor 3 after 24 h of incubation with occurrence of a dose effect (11 µM and 14 µM for respective pyridoxine concentrations of 2 mM and 4 mM). These results show that an incubation of a RC suspension encapsulating a PLP enzyme dependent on PLP with pyridoxine (PN) is capable of increasing the intracellular PLP level in a long lasting way.

EXAMPLE 8

Pharmacokinetics of RC Encapsulating MGL-PLP in Mice

The murine products RC-MGL-PLP2, RC-MGL-PLP3, RC-MGL-PLP4 and RC-MGL-PLP5 are labeled with CFSE (fluorescent) and injected intravenously into CD1 mice.

After various times (D0+15 min, D1, D2, D5, for the three products with additionally D14 and D28 for the RC-MGL-PLP4 and D14 for the RC-MGL-PLP5 product), the mice are sacrificed and the blood is collected on a lithium heparinate tube kept at +4° C. away from light for determining the pharmacokinetics. The proportion of red blood cells labeled with CFSE in the whole blood is determined by a flow cytometry method. Five microliters of whole blood are diluted in 1 ml of PBS 0.5% BSA and each sample is passed in triplicate (counting of 10,000 cells in FL-1; cytometer FC500, Beckman Coulter). The evaluation of the survival of red blood cells loaded with MGL is obtained by adding the proportion of RCs labeled with CFSE at different times to the proportion of RCs labeled with CFSE at T0+15 min (100% control). The different obtained percentages for each time are copied onto a graph (FIG. 4) illustrating the proportion of RCs loaded with MGL in circulation versus time.

The determination of the proportion of RCs marked with CFSE in circulating blood at different times shows its excellent stability of the four products in vivo in mice, up to 120 h post-injection (83.5±0.6%, 94.7±0.6%, 87.3±5.6% and 76.8±1.3% survival rate, respectively). For the product RC-MGL-PLP4, the pharmacokinetic study over 29 days showed that the half-life of the red blood cells encapsulating MGL is ~12.6 days.

EXAMPLE 9

L-Methionine Depletion at 24 h

The murine products RC-MGL-PLP1, RC-MGL-PLP2 and RC-MGL-PLP3 prepared and characterized as in Example 2 are injected intravenously to CD1 mice at a dose of 8 ml/kg. After 6 h, ~0.09 mg of pyridoxine (i.e. 150 µL of a 2.9 mM pyridoxine hydrochloride solution) were injected to mice receiving RC-MGL-PLP2. The L-Met plasma level was evaluated at 24 h by HPLC-MS-MS (Piraud M. et al., Rapid Commun. Mass Spectrum. 19, 3287-97, 2005). The following table shows the depletions obtained in the various groups of injected mice.

| Administered product | Methods for providing the PLP co-enzyme | L-Met plasma level (µM) | % of depletion |
|---|---|---|---|
| — | Feeding | 82.7 ± 22.5 | — |
| RC-MGL-PLP1 | Feeding<br>PLP in the finished product (~5 µmol/l, RC)<br>PLP in the preservation solution of the finished product (10 µM) | 46.3 ± 3.5 | 44% |
| RC-MGL-PLP2 + pyridoxine | Feeding<br>PLP encapsulated in the finished product (~13.4 µmol/l RC)<br>IV injection of ~0.09 mg of pyridoxine | 22.3 ± 4.9 | 73% |
| RC-MGL-PLP3 | Feeding<br>PLP encapsulated in the finished product (~71.4 µmol/l RC) | 29.7 ± 4.6 | 64% |

The L-Met plasma level was evaluated to be 82.7±22.5 µM in control mice. The product RC-MGL-PLP1 containing encapsulated MGL with a low PLP concentration leads to 44% depletion of L-Met, 24 h after administration of the product. We put forward the assumption that the PLP added into the preservation solution of the product is not available for the enzyme MGL since 1) it is in majority bound to the BSA present in the preservation solution and 2) it cannot pass through the membrane of the RC.

The results show that a more consequent provision of PLP in the red corpuscle either by IV injection of pyridoxine (RC-MGL-PLP2) or by encapsulation of PLP at a stronger concentration gives the possibility of obtaining L-Met depletions ~1.5 times greater (73% and 64% depletion respectively).

EXAMPLE 10

Pharmacodynamics of RC-MGLs

The MGL enzyme in its free form is injected intravenously to CD1 mice at a dose of 8 ml/kg. Two series of injections were made, the first with an enzyme concentration at 0.45 mg/ml (product MGL-L1), the second at a twice higher concentration (0.90 mg/ml; product MGL-L2). Six hours after injection, ~0.09 mg of pyridoxine (i.e. 150 µL of a 2.9 mM pyridoxine hydrochloride solution) are injected into mice receiving MGL-L1 and MGL-L2. The L-Met plasma level is evaluated by HPLC-MS-MS at 15 min, 24 h, 48 h, and 120 h post-injection of MGL-L1 and at 15 min, 24 h, 48 h, 120 h and 144 h post-injection of MGL-L2. FIG. 5 shows the depletions obtained in the various groups of injected mice.

The results show that in both experimental groups, a very strong L-methionine depletion (≈4 µM) and rapid overtime (15 min post-injection). However, this depletion is transient and not maintained over time, the L-methionine levels returning into the control values 24 h after injection, and this in spite of the initial provision of P5P (present in the dilution buffer but also in the formulation of the enzyme taken up in water) and the supplementation with vitamin B6 identical with the one carried out for the RC-MGL-PLP2 product. The activity of free MGL is therefore lost between 15 min and 24 h post-injection, probably due to rapid removal of the circulating enzyme.

In a second phase, the murine products RC-MGL-PLP2 and RC-MGL-PLP3 prepared and characterized as in Example 2 are injected intravenously to CD1 mice at a dose of 8 ml/kg. After 6 h, ~0.09 mg of pyridoxine (i.e. 150 µL of a 2.9 mM pyridoxine hydrochloride solution) are injected into the mice receiving RC-MGL-PLP2. The L-Met plasma level is evaluated to be at 15 min, 24 h, 48 h, and 120 h post-injection by HPLC-MS-MS. FIG. 6 and the following table show the depletion obtained in the various groups of injected mice.

The results show that in both experimental groups, an L-methionine depletion stabilized at ~35 µM and maintained over time (from 48 to 120 h post injection). These results indicate that supplementation with PLP or with its precursor (vitamin B6) gives the possibility of maintaining an activity of the MGL encapsulated in RCs for at least 120 h after injection in mice. As an indication, the L-methionine concentrations in plasma 24 and 120 h post-injection for the various products (free form of MGL or co-encapsulated in red blood cells with PLP) are given in the following table:

|  |  | L-methionine level (µM) | | |
|---|---|---|---|---|
|  |  | At T0 (ctrl) | At 24 h | At 120 h |
| Free MGL | MGL-L1 | 68.2 ± 21.7 | 57.0 ± 8.0 | 62.5 ± 12.0 |
|  | MGL-L2 | 68.2 ± 21.7 | 57.3 ± 5.1 | 51.0 ± 8.5 |
| Encapsulated MGL | RC-MGL-PLP2 | 82.7 ± 22.5 | 29.7 ± 4.6 | 36.0 ± 2.6 |
|  | RC-MGL-PLP3 | 82.7 ± 22.5 | 22.3 ± 4.9 | 34.3 ± 7.4 |

In order to assess the pharmacodynamics over times of more than 120 h, the murine product RC-MGL-PLP4 having a concentration of encapsulated MGL of 0.5 mg/ml of enzyme in the finished product is injected intravenously to CD1 mice with a dose of 10 ml/kg. After 6 h, ~0.09 mg of pyridoxine (i.e. 150 µL of a 2.9 mM pyridoxine hydrochloride solution) are injected into the mice receiving RC-MGL-PLP4. The L-Met plasma level is evaluated by HPLC-MS-MS. FIG. 7 shows the depletions obtained at 15 min, on D1, D2, D5, D14 and D28 after injection.

The results show a significant L-methionine depletion (≈10 µM against ≈68 µM for the control) and rapid depletion over time (15 min post-injection). However, this depletion is slightly stabilized between 24 h and 48 h to a value of ~25 µM and increases up to ~40 µM after 5 days so as to finally attain the control values at about 12 days after injection of RC-MGL-PLP4.

Finally, the residual activity of the injected MGL enzyme is determined according to the assay method described in Example 4 in the presence of PLP. FIG. 8 hereafter lists the residual activities versus time for the free enzyme MGL-L2, the various products RC-MGL-PLP and for the TPL enzyme (data from the literature).

The results show that by encapsulating MGL in murine red blood cells it is possible to retain strong enzymatic activity at 24 h (residual activity comprised between ~60 and 100%). This residual activity slightly decreases at 48 h (~35 to 100%) and is maintained up to 120 h, i.e. 5 days after injection, at values comprised between ~20 and ~65%. The residual activity of the MGL in its free form drastically drops in the first minutes post-injection so as to be almost zero at 24 h (residual activity<10%). By comparison, the residual activity of the TPL injected in its free form is copied on the graph and 5 h after injection, the latter is only at most 37% (Elmer et al., 1978). The measurement of the residual activity clearly shows the benefit of encapsulation of the PLP enzymes in red blood cells for maintaining their enzymatic activity.

The invention claimed is:

1. A therapeutic treatment method for depleting or reducing a plasma or circulating substrate selected from the group consisting of methionine, homocysteine and tyrosine in a patient in need thereof comprising administering an effective amount of a composition comprising erythrocytes encapsulating a pyridoxal phosphate (PLP)-dependent enzyme and administering an effective amount of a non-phosphate form of vitamin B6, wherein the composition and the non-phosphate form of vitamin B6 are administered separately or sequentially;
    wherein the administration of the effective amount of the non-phosphate form of vitamin B6 and the effective amount of the encapsulated PLP-dependent enzyme produces greater residual PLP-dependent enzyme activity than administration of the same amount of the vitamin B6 and the same amount of a non-encapsulated, free form of the PLP-dependent enzyme.

2. A therapeutic treatment method for depleting or reducing a plasma or circulating substrate selected from the group consisting of methionine, homocysteine and tyrosine in a patient in need thereof, comprising:
    a) administering an effective amount of a composition comprising erythrocytes and a pharmaceutically acceptable vehicle, the erythrocytes encapsulating a PLP-dependent enzyme and pyridoxal phosphate (PLP), and
    b) administering a non-phosphate form of vitamin B6 in an amount effective to maintain the encapsulated PLP-dependent enzyme in its holoenzyme form longer relative to the same PLP-dependent enzyme not encapsulated in erythrocytes;
wherein the composition and the non-phosphate form of vitamin B6 are administered separately or sequentially.

3. The method according to claim 2, wherein the patient in need thereof is a patient suffering from cancer.

4. The method according to claim 3, wherein said cancer comprises tumoral cells auxotrophic for methionine or tyrosine and the PLP-dependent enzyme is selected from the group consisting of methioninase and tyrosine phenol-lyase.

5. The method according to claim 2, wherein the patient in need thereof is a patient suffering from Richner-Hanhart syndrome (tyrosinemia type II) and the PLP-dependent enzyme is tyrosine aminotransferase.

6. The method of claim 1, wherein the composition comprising the erythrocytes is injected, and the composition comprising the non-phosphate form of vitamin B6 is administered by an oral route.

7. The method of claim 1, wherein the concentration of the PLP-dependent enzyme encapsulated in the erythrocytes is from 0.05 to 600 µmol.

8. The method of claim 1, wherein the PLP-dependent enzyme is a methioninase.

9. The method of claim 8, wherein the methioninase is methionine gamma lyase (MGL).

10. The method of claim 9, wherein the substrate is methionine, and wherein the depletion of the substrate is sufficient to treat cancer.

11. The method of claim 1, wherein the non-phosphate form of vitamin B6 is selected from the group consisting of pyridoxal, pyridoxine, pyridoxamine, and mixtures thereof.

12. The method of claim 11, wherein the non-phosphate form of vitamin B6 is pyridoxine.

13. The method of claim 1, wherein the residual PLP-dependent enzyme activity persists for at least about 1 day post administration of the encapsulated PLP-dependent enzyme and the vitamin B6.

14. The method of claim 13, wherein the activity persists for at least about 2 days post administration of the encapsulated PLP-dependent enzyme and the vitamin B6.

15. The method of claim 14, wherein the activity persists for at least about 5 days post administration of the encapsulated PLP-dependent enzyme and the vitamin B6.

* * * * *